(12) United States Patent
Tedesco

(10) Patent No.: US 11,491,398 B2
(45) Date of Patent: Nov. 8, 2022

(54) METHODS AND SYSTEMS FOR INCREASING ATTENTION ABILITY OF A USER USING A GAMEPLAY

(71) Applicant: Charles Tedesco, Patchogue, NY (US)

(72) Inventor: Charles Tedesco, Patchogue, NY (US)

( * ) Notice: Subject to any disclaimer, the term of this patent is extended or adjusted under 35 U.S.C. 154(b) by 196 days.

(21) Appl. No.: 17/001,513

(22) Filed: Aug. 24, 2020

(65) Prior Publication Data

US 2022/0054942 A1 Feb. 24, 2022

(51) Int. Cl.
| | |
|---|---|
| *A63F 13/54* | (2014.01) |
| *A63F 13/46* | (2014.01) |
| *A63F 13/2145* | (2014.01) |
| *A63F 13/44* | (2014.01) |
| *A63F 13/212* | (2014.01) |
| *A63F 13/80* | (2014.01) |
| *A61B 5/16* | (2006.01) |
| *A63F 13/211* | (2014.01) |
| *A61B 5/369* | (2021.01) |

(52) U.S. Cl.
CPC .............. *A63F 13/54* (2014.09); *A61B 5/163* (2017.08); *A61B 5/369* (2021.01); *A63F 13/211* (2014.09); *A63F 13/212* (2014.09); *A63F 13/2145* (2014.09); *A63F 13/44* (2014.09); *A63F 13/46* (2014.09); *A63F 13/80* (2014.09); *A61B 2503/12* (2013.01); *A63F 2300/105* (2013.01); *A63F 2300/1012* (2013.01); *A63F 2300/1075* (2013.01); *A63F 2300/6081* (2013.01); *A63F 2300/61* (2013.01); *A63F 2300/638* (2013.01); *A63F 2300/8094* (2013.01)

(58) Field of Classification Search
CPC ........ A63F 2300/1012; A63F 2300/105; A63F 2300/1075; A63F 2300/6081; A63F 2300/61; A63F 2300/638; A63F 2300/8094; A63F 13/35; A63F 13/80; A63F 13/211; A63F 13/212; A63F 13/2145; A63F 13/44; A63F 13/46; A63F 13/54; A61B 2503/12; A61B 5/369
See application file for complete search history.

(56) References Cited

U.S. PATENT DOCUMENTS

| | | | |
|---|---|---|---|
| 2013/0172081 A1* | 7/2013 | Shiina | A63F 13/54 463/31 |
| 2016/0246498 A1* | 8/2016 | Rav-Noy | G06F 3/04883 |
| 2019/0216392 A1* | 7/2019 | Bower | G16H 50/20 |

* cited by examiner

*Primary Examiner* — James S. McClellan
*Assistant Examiner* — Ross A Williams

(57) ABSTRACT

Disclosed is a system for increasing attention ability of a user using a gameplay. The system may include a display device configured to display a moving image comprising an object, a cursor and a points counter. Further, the system may include an audio device configured to produce acoustic waves based on a sound data associated with a level. Further, the system may include an input device configured to receive a spatial input data. Further, the system may include a processing device communicatively coupled to each of the display device, the audio device and the input device. Further, the system may include a storage device communicatively coupled to the processing device. Further, the storage device may be configured to store digital data corresponding to an object, a cursor, a current cursor location, a previous cursor location, a geometric shape and the sound data in association with the multiple level indicators.

18 Claims, 25 Drawing Sheets

Game Instructions:

- Hover mouse on top of white ball.

- Trace geometric shape while following white ball.

- Gain points while moving along path.

- Finish part (or entire) figure to gain a lap.

Back

FIG. 23

Tedesco Art Inc.
Email:
tedescoart@gmail.com
Phone: (6331) 406-3457

Back

FIG. 24

METHODS AND SYSTEMS FOR INCREASING ATTENTION ABILITY OF A USER USING A GAMEPLAY

FIELD OF THE INVENTION

Generally, the present disclosure relates to the field of data processing. More specifically, the present disclosure relates to methods and systems for increasing attention ability of a user using a gameplay.

BACKGROUND OF THE INVENTION

Some studies have shown that the number of children diagnosed with attention-deficit/hyper-activity disorder (ADHD) has reached more than 10 percent, a significant increase during the past 20 years.

Further, the number of children diagnosed with autism or related disorders has grown at what many call an alarming rate. In the 1970s and 1980s, about one out of every 2,000 children had autism. Today, the CDC estimates that one in 150 8-year-olds in the U.S. has an autism spectrum disorder, or ASD.

Some games are known to help children develop focus However, existing games for helping children develop focus are deficient with regard to several aspects. For instance, current games do not use a combination of visual and aural inputs to engage children in game play, wherein the visual and aural inputs are specifically design to help children develop focus. Furthermore, current games do not offer a step-by-step process to improve focus of children suffering from AHDH and/or autism.

Therefore, there is a need for improved methods and systems for increasing attention ability of a user using a gameplay that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a system for increasing attention ability of a user using a gameplay. The system may include a display device configured to display a moving image comprising an object, a cursor and a points counter. Further, the object may traverse along at least one geometric shape of a plurality of geometric shapes at a predetermined speed and along a predetermined direction. Further, the geometric shape may correspond to a level of a plurality of levels of the gameplay. Further, the displaying of the moving image may be based on a video data. Further, the system may include an audio device configured to produce acoustic waves based on a sound data associated with the level. Further, the production of acoustic waves may be synchronous with the display of the moving image. Further, the system may include an input device configured to receive a spatial input data. Further, the system may include a processing device communicatively coupled to each of the display device, the audio device and the input device. Further, the processing device may be configured to generate the video data and the sound data based on a level indicator of a plurality of level indicators associated with the level and the spatial input data. Further, the processing device may be configured to determine a current cursor location associated with the cursor based on each of the spatial input data and a previous cursor location associated with the cursor. Further, each of the current cursor location, the previous cursor location and the spatial input is in relation to a coordinate frame associated with the moving image. Further, the processing device may be configured to determine a current object location associated with the object. Further, the object location may be in relation to the coordinate frame associated with the moving image. Further, the processing device may be configured to determine a distance data representing a distance between the object and the cursor based on a difference between the current cursor location and the current object location. Further, the processing device may be configured to analyze the distance data. Further, the processing device may be configured to increment a points counter data associated with the points counter based on the analysis of the distance data. Further, the processing device may be configured to determine a next object location of the object based on the analysis of the distance data. Further, the next object location may be in relation to a coordinate frame associated with the moving image. Further, the processing device may be configured to generate the sound data based on the analysis of the distance data. Further, the system may include a storage device communicatively coupled to the processing device. Further, the storage device may be configured to store digital data corresponding to the object, the cursor, the current cursor location, the previous cursor location, the at least one geometric shape and the sound data in association with the plurality of level indicators.

According to some embodiments, a system for increasing attention ability of a user using a gameplay is disclosed. The system may include a display device configured to display a moving image comprising an object, a cursor and a points counter. Further, the object may traverse along at least one geometric shape of a plurality of geometric shapes at a predetermined speed and along a predetermined direction. Further, the geometric shape may correspond to a level of a plurality of levels of the gameplay. Further, the displaying of the moving image may be based on a video data. Further, the system may include an audio device configured to produce acoustic waves based on a sound data associated with the level. Further, the production of acoustic waves may be synchronous with the display of the moving image. Further, the system may include an input device configured to receive a spatial input data. Further, the system may include an EEG sensor configured to generate EEG data of the user. Further, the system may include a processing device communicatively coupled to each of the display device, the audio device and the input device. Further, the processing device may be configured to generate the video data and the sound data based on a level indicator of a plurality of level indicators associated with the level and the spatial input data. Further, the processing device may be configured to determine a current cursor location associated with the cursor based on each of the spatial input data and a previous cursor location associated with the cursor. Further, each of the current cursor location, the previous cursor location and the spatial input may be in relation to a coordinate frame associated with the moving image. Further, the processing device may be configured to determine a current object location associated with the object. Further, the object location may be in relation to the coordinate frame associated with the moving image. Further, the processing device may be configured to determine a distance data representing a distance between the object and the cursor based on a difference between the current cursor location and the current object location. Further, the processing device may be configured to analyze the distance data. Further, the processing device may be configured to increment a points counter data associated with the points counter based on the analysis of the distance data. Further, the processing device may be configured to determine a next object location of the object based on the analysis of the distance data. Further, the next object location may be in relation to a coordinate frame associated with the moving image. Further, the processing device may be configured to generate the sound data based on the analysis of the distance data. Further, the processing device may be configured to analyze the EEG data. Further, the processing device may be configured to determine an attention level of the user based on the analysis of the EEG data. Further, the processing device may be configured to determining the level indicator of the gameplay based on the attention level of the user. Further, the system may include a storage device communicatively coupled to the processing device. Further, the storage device is configured to store digital data corresponding to the object, the cursor, the current cursor location, the previous cursor location, the at least one geometric shape and the sound data in association with the plurality of level indicators.

According to some embodiments, a system for increasing attention ability of a user using a gameplay is disclosed. The system may include a display device configured to display a moving image comprising an object, a cursor and a points counter. Further, the object traverses along at least one geometric shape of a plurality of geometric shapes at a predetermined speed and along a predetermined direction. Further, the geometric shape may correspond to a level of a plurality of levels of the gameplay. Further, the displaying of the moving image may be based on a video data. Further, the system may include an audio device configured to produce acoustic waves based on a sound data associated with the level. Further, the production of acoustic waves may be synchronous with the display of the moving image. Further, the audio device may be configured to generate acoustic waves over a plurality of frequencies comprising 256 Hz, 288 Hz, 323 Hz, 343 Hz, 385 Hz, 432 Hz and 484 Hz respectively corresponding to the plurality of levels of the gameplay. Further, the system may include an input device configured to receive a spatial input data. Further, the system may include a processing device communicatively coupled to each of the display device, the audio device and the input device. Further, the processing device may be configured to generate the video data and the sound data based on a level indicator of a plurality of level indicators associated with the level and the spatial input data. Further, the processing device may be configured to determine a current cursor location associated with the cursor based on each of the spatial input data and a previous cursor location associated with the cursor. Further, each of the current cursor location, the previous cursor location and the spatial input may be in relation to a coordinate frame associated with the moving image. Further, the processing device may be configured to determine a current object location associated with the object. Further, the object location may be in relation to the coordinate frame associated with the moving image. Further, the processing device may be configured to determine a distance data representing a distance between the object and the cursor based on a difference between the current cursor location and the current object location. Further, the processing device may be configured to analyze the distance data. Further, the processing device may be configured to increment a points counter data associated with the points counter based on the analysis of the distance data. Further, the processing device may be configured to determine a next object location of the object based on the analysis of the distance data. Further, the next object location may be in relation to a coordinate frame associated with the moving image. Further, the processing device may be configured to generate the sound data based on the analysis of the distance data. Further, the system may include a storage device communicatively coupled to the processing device. Further, the storage device may be configured to store digital data corresponding to the object, the cursor, the current cursor location, the previous cursor location, the at least one geometric shape and the sound data in association with the plurality of level indicators.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

FIG. 23 is instruction user interface of the game, in accordance with exemplary embodiments.

FIG. 24 is credits user interface of the game, in accordance with exemplary embodiments.

DETAILED DESCRIPTION OF THE INVENTION

Figure 1:
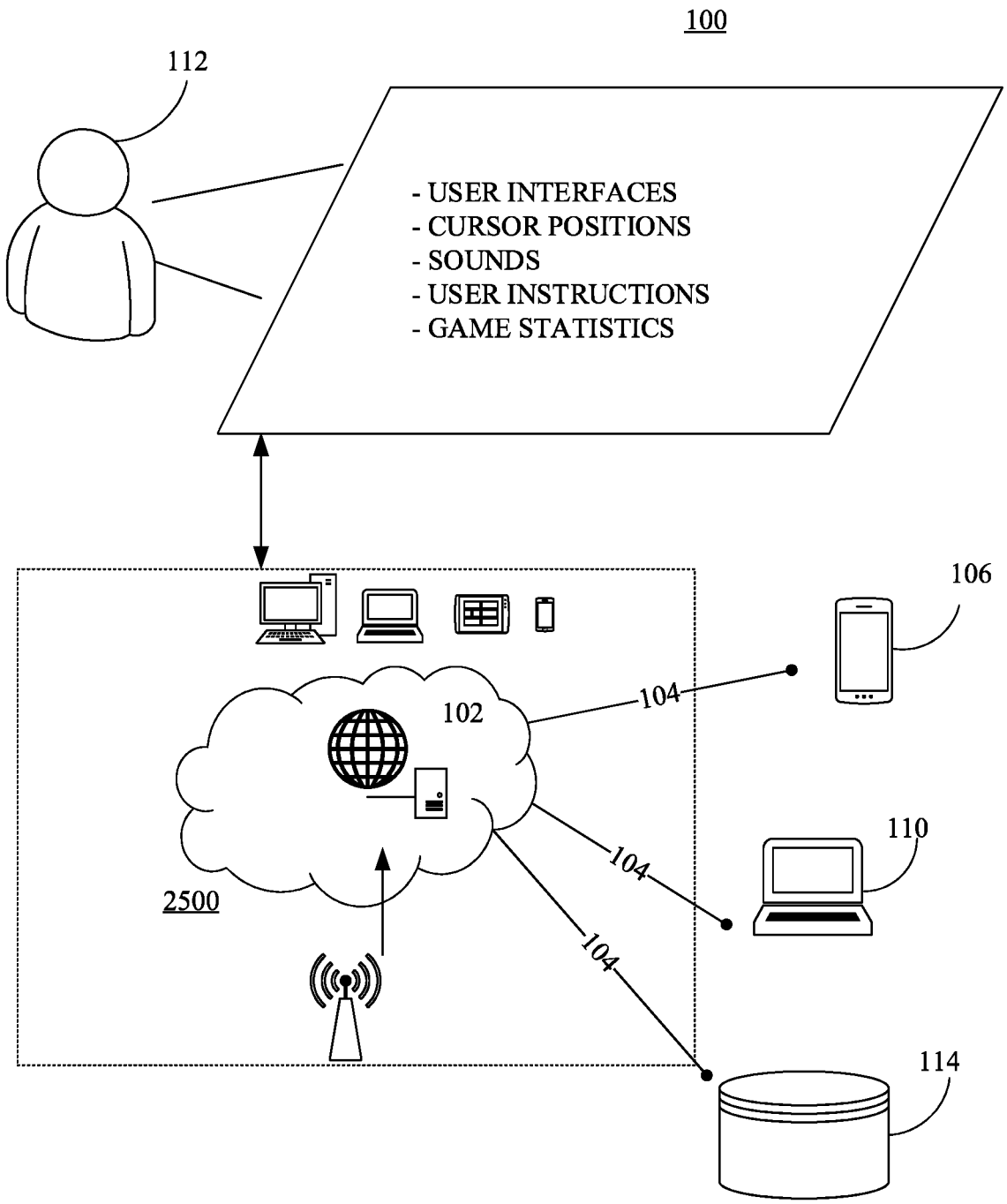
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods and systems for increasing attention ability of a user using a gameplay, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps.

For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

FIG. 1 is an illustration of an online platform 100 consistent with various embodiments of the present disclosure. By way of non-limiting example, the online platform 100 to facilitate increasing attention ability of a user using a gameplay may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114 over a communication network 104, such as, but not limited to, the Internet. Further, users of the online platform 100 may include relevant parties such as, but not limited to, end-users (game players), administrators, service providers, service consumers and so on. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 2500.

Figure 2:
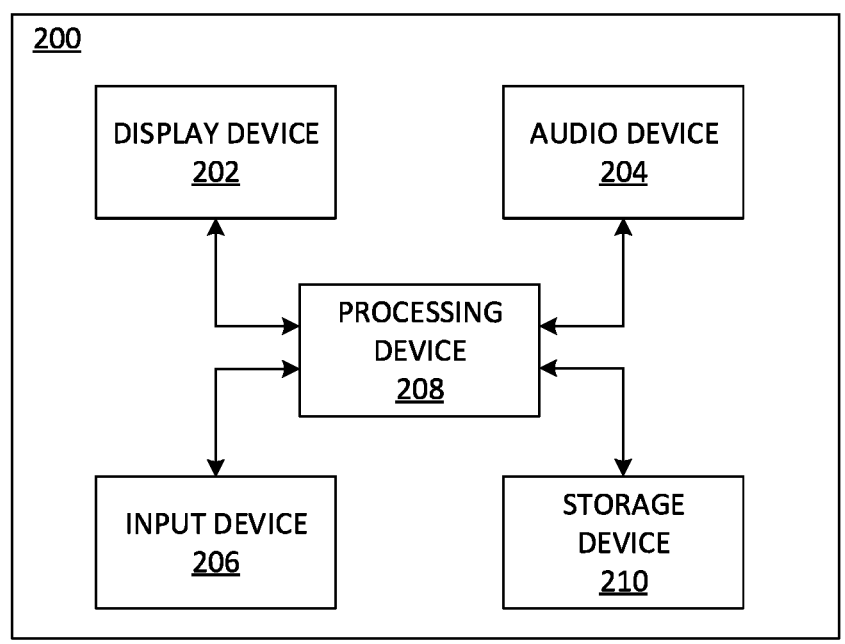
FIG. 2 is a block diagram of a system for increasing attention ability of a user using a gameplay, in accordance with some embodiments.

FIG. 2 is a block diagram of a system 200 for increasing attention ability of a user using a gameplay, in accordance with some embodiments. The system 200 may include a display device 202 configured to display a moving image comprising an object, a cursor and a points counter. Further, the object may traverse along at least one geometric shape of a plurality of geometric shapes at a predetermined speed and along a predetermined direction. Further, the geometric shape may correspond to a level of a plurality of levels of the gameplay. Further, the displaying of the moving image may be based on a video data.

In some embodiments, the moving image may include a visual rendering of the at least one geometric shape.

Further, the system 200 may include an audio device 204 configured to produce acoustic waves based on a sound data associated with the level. Further, the production of acoustic waves may be synchronous with the display of the moving image.

In some embodiments, the audio device may be configured to generate acoustic waves over a plurality of frequencies comprising 256 Hz, 288 Hz, 323 Hz, 343 Hz, 385 Hz, 432 Hz and 484 Hz respectively corresponding to the plurality of levels of the gameplay.

Further, the system 200 may include an input device 206 configured to receive a spatial input data. In some embodiments, the input device may include an inertial sensor configured to generate the spatial input data based on a motion imparted to the input device. In some embodiments, the input device may include at least one of a mouse, a trackpad and a joy-stick. In some embodiments, the input device may include a gaze tracking device configured to detect a gaze of the user in relation to the coordinate frame associated with the moving image, wherein the spatial input is based on the gaze.

Further, the system 200 may include a processing device 208 communicatively coupled to each of the display device 202, the audio device 204 and the input device 206. Further, the processing device 208 may be configured to generate the video data and the sound data based on a level indicator of a plurality of level indicators associated with the level and the spatial input data.

Further, the video data may include pixel values associated with a plurality of pixels. Further, each of a plurality of object pixels and a plurality of object pixel values may be associated with the object. Further, each of a plurality of cursor pixels and a plurality of cursor pixel values may be associated with the cursor, wherein the plurality of object pixels is associated with an object location based on a location of a reference object pixel of the plurality of object pixels in relation to a coordinate frame. Further, the plurality of cursor pixels may be associated with a cursor location based on a cursor location of a cursor pixel of the plurality of cursor pixels in relation to the coordinate frame.

Further, the processing device 208 may be configured to determine a current cursor location associated with the cursor based on each of the spatial input data and a previous cursor location associated with the cursor. Further, each of the current cursor location, the previous cursor location and the spatial input is in relation to a coordinate frame associated with the moving image.

Further, the processing device 208 may be configured to determine a current object location associated with the object. Further, the object location may be in relation to the coordinate frame associated with the moving image.

Further, the processing device 208 may be configured to determine a distance data representing a distance between the object and the cursor based on a difference between the current cursor location and the current object location.

Further, the processing device 208 may be configured to analyze the distance data. In some embodiments, the analysis of the distance data may include comparing the distance data with a predetermined threshold. Further, the next object location of the object may be determined to be the current object location based on the distance data being greater the predetermined threshold. Further, the processing device 208 may cease to generate the sound based on the distance data being greater the predetermined threshold. In other words, if the distance data indicates that the cursor did not follow the object within the threshold limit, the object does not move to the next location but stays in its current location.

Further, the processing device 208 may be configured to increment a points counter data associated with the points counter based on the analysis of the distance data.

Further, the processing device 208 may be configured to determine a next object location of the object based on the analysis of the distance data. Further, the next object location may be in relation to a coordinate frame associated with the moving image.

Further, the processing device 208 may be configured to generate the sound data based on the analysis of the distance data.

Further, the system 200 may include a storage device 210 communicatively coupled to the processing device 208. Further, the storage device 210 may be configured to store digital data corresponding to the object, the cursor, the current cursor location, the previous cursor location, the at least one geometric shape and the sound data in association with the plurality of level indicators.

In further embodiments, the processing device 208 may be configured to select the predetermined speed from a plurality of predetermined speeds based on a speed control input. Further, the input device may be configured to receive the speed control input.

In further embodiments, the processing device 208 may be configured to determine laps data representing a number of laps associated with the traversal of the object along the at least one geometrical shape. Further, the display device may be configured to display a laps counter based on the laps data.

In some embodiments, the moving image may include a leading object positioned ahead of the object along a direction of the traversal, wherein the leading object traverses the at least one geometric shape.

In further embodiments, the moving image may include the leading object for a predetermined time duration from a start the gameplay. Further, the leading object may fade away subsequent to elapse of the predetermined time duration. Further, the processing device 208 may be configured to fade away the leading object based on a fade mode input received from the input device 206.

In some embodiments, the processing device 208 may be configured to generate the video data and the sound data for a predetermined duration of the gameplay. Further, the predetermined duration of the gameplay may be based on a program time input received from the input device 206.

In further embodiments, the processing device 208 may be configured to generate the video data comprising a countdown timer based on timer data. Further, the processing device 208 may be configured for generate the timer data based on time elapsed since beginning of the gameplay.

In some embodiments, the processing device 208 may be configured to generate a simulation mode video data corresponding to the level of the gameplay. Further, the generation of the simulation mode vide data may be based on a simulation mode control input received from the input device 206. Further, the object corresponding to the simulation mode video data may automatically traverse the at least one geometric shape independent of the spatial input data received subsequent to receiving the simulation mode control input. Further, the processing device 208 may be configured to generate the sound data independent of the spatial input data received subsequent to receiving the simulation mode control input.

Figure 3:
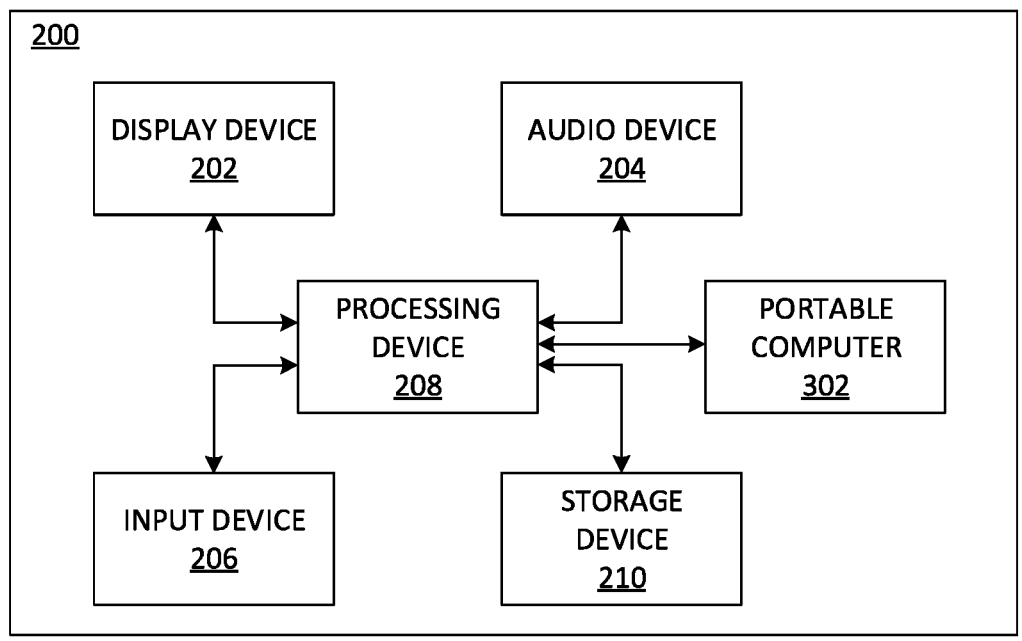
FIG. 3 is a block diagram of a system for increasing attention ability of a user using a gameplay, in accordance with further embodiments.

FIG. 3 is a block diagram of the system 200 for increasing attention ability of a user using a gameplay, in accordance with further embodiments. The system 200 may further include a portable computer 302. Further, each of the display device 202 and the input device 206 may comprise in a touchscreen of the portable computer 302.

Figure 4:
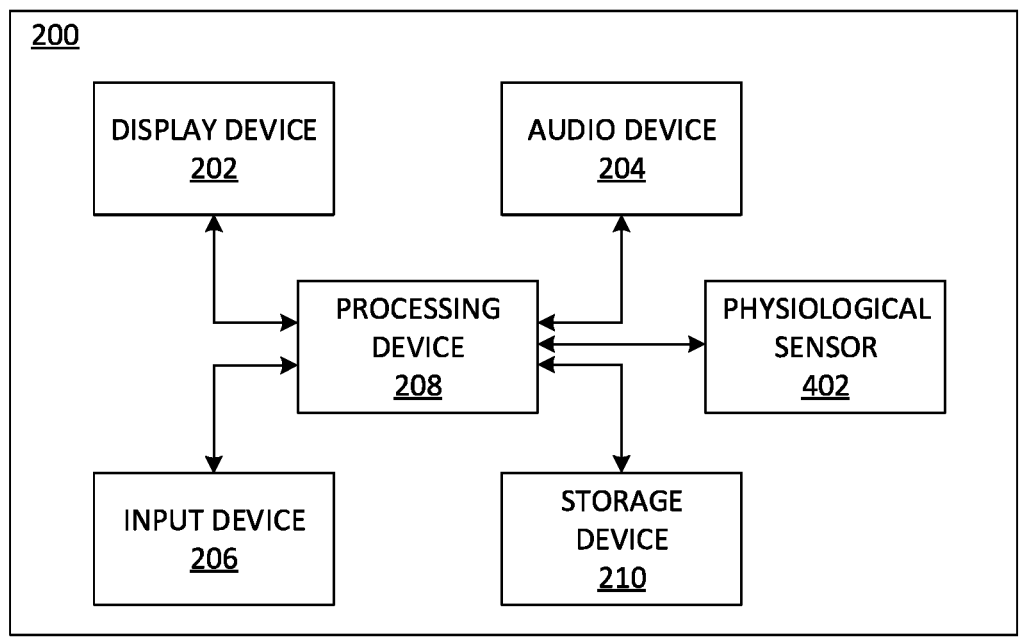
FIG. 4 is a block diagram of a system for increasing attention ability of a user using a gameplay, in accordance with further embodiments.

FIG. 4 is a block diagram of the system 200 for increasing attention ability of a user using a gameplay, in accordance with further embodiments. The system 200 may further include a physiological sensor 402 configured to generate a physiological data of the user. Further, the physiological sensor may be communicatively coupled to the processing device 208. Further, the processing device 208 may be configured to select at least one of the object, the cursor, the at least one geometric shape, the predetermined direction, the predetermined speed and the sound data based on the physiological data.

In further embodiments, the physiological sensor 402 may include an EEG sensor, wherein the physiological data comprises EEG data. Further, the processing device 208 may be configured to analyze the EEG data and determine an attention level of the user based on the analysis of the EEG data, wherein the selection of at least one of the object, the cursor, the at least one geometric shape, the predetermined direction, the predetermined speed and the sound data is based on analysis of the EEG data.

Figure 5:
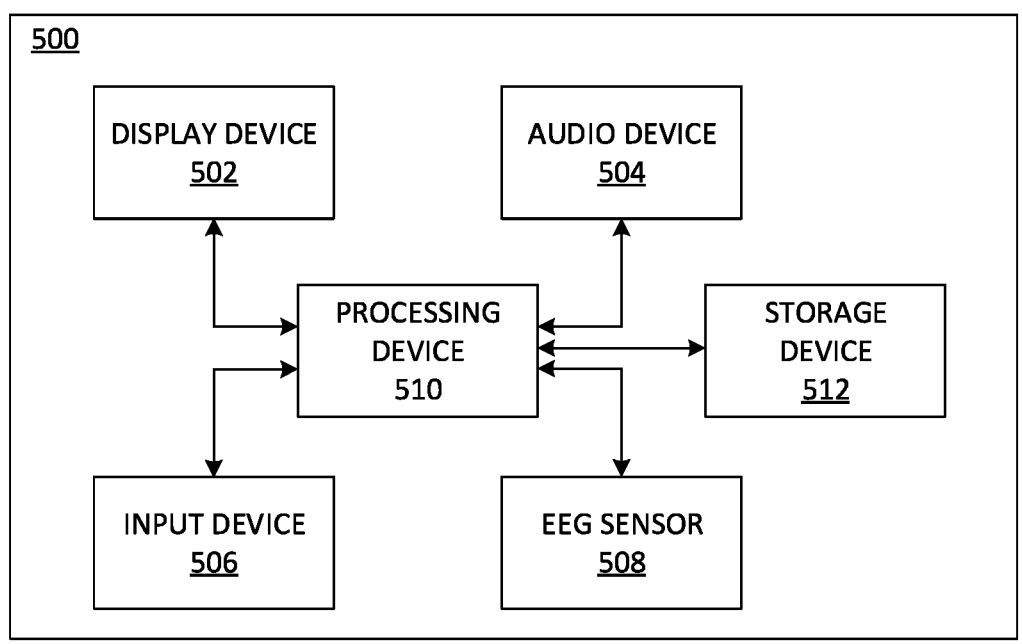
FIG. 5 is a block diagram of a system for increasing attention ability of a user using a gameplay, in accordance with some embodiments.

FIG. 5 is a block diagram of a system 500 for increasing attention ability of a user using a gameplay, in accordance with some embodiments. The system 500 may include a a display device 502 configured to display a moving image comprising an object, a cursor and a points counter. Further, the object may traverse along at least one geometric shape of a plurality of geometric shapes at a predetermined speed and along a predetermined direction. Further, the geometric shape may correspond to a level of a plurality of levels of the gameplay. Further, the displaying of the moving image may be based on a video data.

In some embodiments, the video data may include pixel values associated with a plurality of pixels, wherein each of a plurality of object pixels and a plurality of object pixel values is associated with the object. Further, each of a plurality of cursor pixels and a plurality of cursor pixel values is associated with the cursor. Further, the plurality of object pixels is associated with an object location based on a location of a reference object pixel of the plurality of object pixels in relation to a coordinate frame. Further, the plurality of cursor pixels is associated with a cursor location based on a cursor location of a cursor pixel of the plurality of cursor pixels in relation to the coordinate frame.

Further, the system 500 may include an audio device 504 configured to produce acoustic waves based on a sound data associated with the level. Further, the production of acoustic waves may be synchronous with the display of the moving image.

Further, the system 500 may include an input device 506 configured to receive a spatial input data.

Further, the system 500 may include an EEG sensor 508 configured to generate EEG data of the user.

Further, the system 500 may include a processing device 510 communicatively coupled to each of the display device 502, the audio device 504 and the input device 506.

Further, the processing device 510 may be configured to generate the video data and the sound data based on a level indicator of a plurality of level indicators associated with the level and the spatial input data.

Further, the processing device 510 may be configured to determine a current cursor location associated with the cursor based on each of the spatial input data and a previous cursor location associated with the cursor. Further, each of the current cursor location, the previous cursor location and the spatial input may be in relation to a coordinate frame associated with the moving image.

Further, the processing device 510 may be configured to determine a current object location associated with the object. Further, the object location may be in relation to the coordinate frame associated with the moving image.

Further, the processing device 510 may be configured to determine a distance data representing a distance between the object and the cursor based on a difference between the current cursor location and the current object location.

Further, the processing device 510 may be configured to analyze the distance data.

Further, the processing device 510 may be configured to increment a points counter data associated with the points counter based on the analysis of the distance data.

Further, the processing device 510 may be configured to determine a next object location of the object based on the analysis of the distance data. Further, the next object location may be in relation to a coordinate frame associated with the moving image.

Further, the processing device 510 may be configured to generate the sound data based on the analysis of the distance data.

Further, the processing device 510 may be configured to analyze the EEG data. Further, the processing device 510 may be configured to determine an attention level of the user based on the analysis of the EEG data.

Further, the processing device 510 may be configured to determining the level indicator of the gameplay based on the attention level of the user.

Further, the system 500 may include a storage device 512 communicatively coupled to the processing device 510. Further, the storage device 512 is configured to store digital data corresponding to the object, the cursor, the current cursor location, the previous cursor location, the at least one geometric shape and the sound data in association with the plurality of level indicators.

Figure 6:
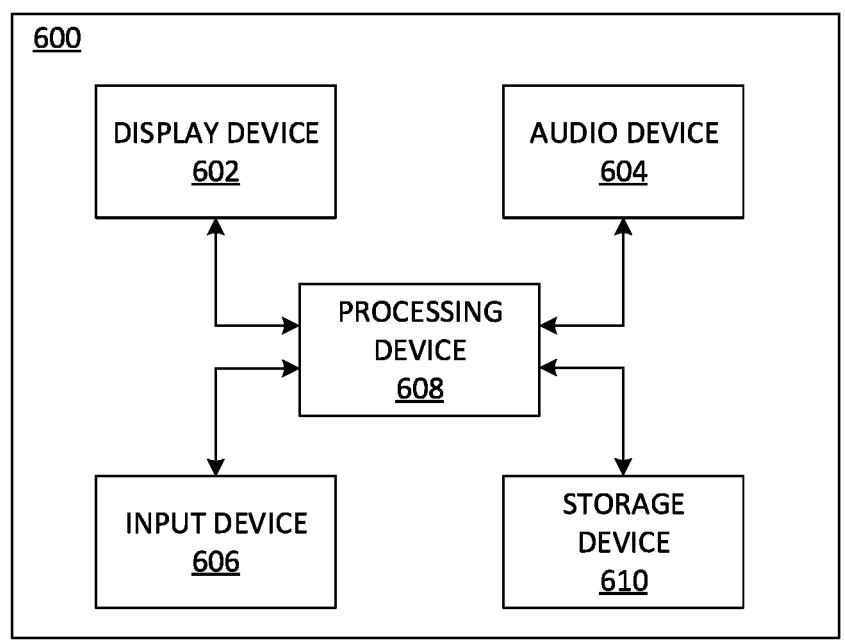
FIG. 6 is a block diagram of a system for increasing attention ability of a user using a gameplay, in accordance with some embodiments.

FIG. 6 is a block diagram of a system 600 for increasing attention ability of a user using a gameplay, in accordance with some embodiments. The system 600 may include a display device 602 configured to display a moving image comprising an object, a cursor and a points counter. Further, the object traverses along at least one geometric shape of a plurality of geometric shapes at a predetermined speed and along a predetermined direction. Further, the geometric shape may correspond to a level of a plurality of levels of the gameplay.

Further, the displaying of the moving image may be based on a video data. In some embodiments, the video data may include pixel values associated with a plurality of pixels, wherein each of a plurality of object pixels and a plurality of object pixel values is associated with the object. Further, each of a plurality of cursor pixels and a plurality of cursor pixel values is associated with the cursor. Further, the plurality of object pixels is associated with an object location based on a location of a reference object pixel of the plurality of object pixels in relation to a coordinate frame. Further, the plurality of cursor pixels is associated with a cursor location based on a cursor location of a cursor pixel of the plurality of cursor pixels in relation to the coordinate frame.

Further, the system 600 may include an audio device 604 configured to produce acoustic waves based on a sound data associated with the level. Further, the production of acoustic waves may be synchronous with the display of the moving image. Further, the audio device 604 may be configured to generate acoustic waves over a plurality of frequencies comprising 256 Hz, 288 Hz, 323 Hz, 343 Hz, 385 Hz, 432 Hz and 484 Hz respectively corresponding to the plurality of levels of the gameplay.

Further, the system 600 may include an input device 606 configured to receive a spatial input data.

Further, the system 600 may include a processing device 608 communicatively coupled to each of the display device 602, the audio device 604 and the input device 606.

Further, the processing device 608 may be configured to generate the video data and the sound data based on a level indicator of a plurality of level indicators associated with the level and the spatial input data.

Further, the processing device 608 may be configured to determine a current cursor location associated with the cursor based on each of the spatial input data and a previous cursor location associated with the cursor. Further, each of the current cursor location, the previous cursor location and the spatial input may be in relation to a coordinate frame associated with the moving image.

Further, the processing device 608 may be configured to determine a current object location associated with the object. Further, the object location may be in relation to the coordinate frame associated with the moving image.

Further, the processing device 608 may be configured to determine a distance data representing a distance between the object and the cursor based on a difference between the current cursor location and the current object location.

Further, the processing device 608 may be configured to analyze the distance data. In some embodiments, the analysis of the distance data may include comparing the distance data with a predetermined threshold. Further, the next object location of the object may be determined to be the current object location based on the distance data being greater the predetermined threshold. Further, the processing device 608 may cease to generate the sound data based on the distance data being greater the predetermined threshold.

In other words, if the distance data indicates that the cursor did not follow the object within the threshold limit, the object does not move to the next location but stays in its current location.

Further, the processing device 608 may be configured to increment a points counter data associated with the points counter based on the analysis of the distance data. Further, the processing device 608 may be configured to determine a next object location of the object based on the analysis of the distance data. Further, the next object location may be in relation to a coordinate frame associated with the moving image. Further, the processing device 608 may be configured to generate the sound data based on the analysis of the distance data.

Further, the system 600 may include a storage device 610 communicatively coupled to the processing device 608. Further, the storage device 610 may be configured to store digital data corresponding to the object, the cursor, the current cursor location, the previous cursor location, the at least one geometric shape and the sound data in association with the plurality of level indicators.

According to some embodiments, a software game (Infinity Lightpath) for players to help increase present moment focus and attention, specifically for those classified with Attention Deficit Disorder and or Autism is disclosed. The game may have seven levels to help to increase present moment focus through player physical motor skills (eye and hand coordination) to manage keeping the cursor over a moving white ball that traces different geometric shapes to corresponding tone frequencies. Each of the 7 level different geometric shapes in the game play along with specific crystal bowl/tuning fork sound sampled frequencies for each level. The higher ability to focus benefit in present moment develops from the success of the player being able to stay focused to keep the cursor hovering over a white ball while it moves around and traces a geometric shape while playing a sound frequency for that shape. The player manipulates moving the cursor via mouse or using touchpad to try to keep it hovered over the moving white ball as best as they can without falling off its edges. If the cursor falls off the moving white ball, then points/laps stop earning and the white ball motion is deactivated. Once the player is able to regain hovering cursor over the white ball it's movement is activated and points/laps accumulate in score and lap tally windows. The goal is to earn as many points/laps as possible within a set programmed time frame that counts down to zero to end game. The game also features a simulation mode whereby the player can click on a simulation mode option and set amount of desired time to only watch white ball automatically move/trace along geometric shape while listening to sound frequency audibly playing. This is done without having to physically manipulate hovering cursor over white ball to keep its movement in play. Player will be able to receive therapeutic focus benefits by simply watching and listening to the white ball movement along the geometric shape. Each of the geometric shapes possess a pattern that allows the white ball movement to a centered singularity. The movement and tracing a geometric pattern to singularity creates a higher focus and present moment awareness for the player utilizing the Infinity Lightpath program as these patterns simulate geometric patterns and sound frequencies of nature in the 432 Hz scale. This program was created for players/students to help gain better focus in present moment before performing academic, psychological or physical task. The Infinity Lightpath software platform may be used on PC and Macintosh. The background colors for each of the 7 geometric shapes correlates with the seven fields/layers of the electromagnetic human aura field.

Further, the player must successfully maintain moving the cursor over the moving white ball in the game while it traces the geometric path for that particular level. As the player is able to maintain keeping the cursor over the white ball, it will move along tracing the geometric shape earning points within a manually programmed time frame. The cursor can be moved in the game via a mouse or using touchpad. The goal for the player is to maintain the cursor over the moving white ball as long as possible at programed speed and allocated timeframe earning as many points as possible in each of the seven levels of the game. Successfully maintaining the cursor over the white ball in each of the seven levels forces the player to increase concentration and focus in present moment. Goal would be for the player to accumulate as many laps and highest points possible in a specific amount of time that was programmed to play. Also the rate of speed by which player is able to maintain play of the cursor hovered over white ball determines number of points/ laps earned. Gameplay of white ball traveling stops when cursor is not maintained hovering over it (which ceases earning of points/laps). When cursor is re-engaged hovering over the white ball it will then continue to resume travel and earn points/laps.

Figure 7:
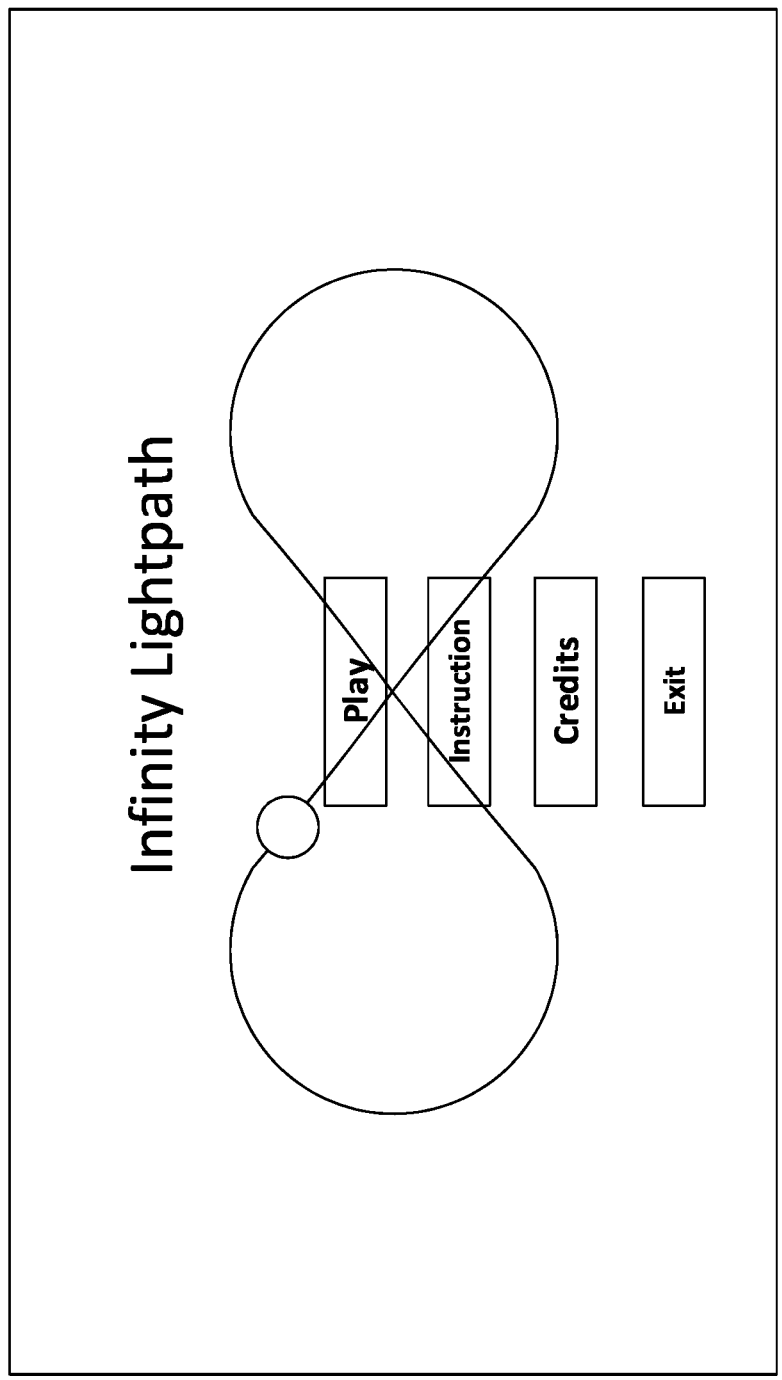
FIG. 7 is introduction user interface of the game, in accordance with exemplary embodiments.

FIG. 7 is introduction user interface of the game, in accordance with exemplary embodiments. The introduction user interface includes Infinity Lightpath Title, Background image of infinity sign, four buttons including to "Play" button, "Instructions" button, "Credits" button and "Exit" button.

Figure 8:
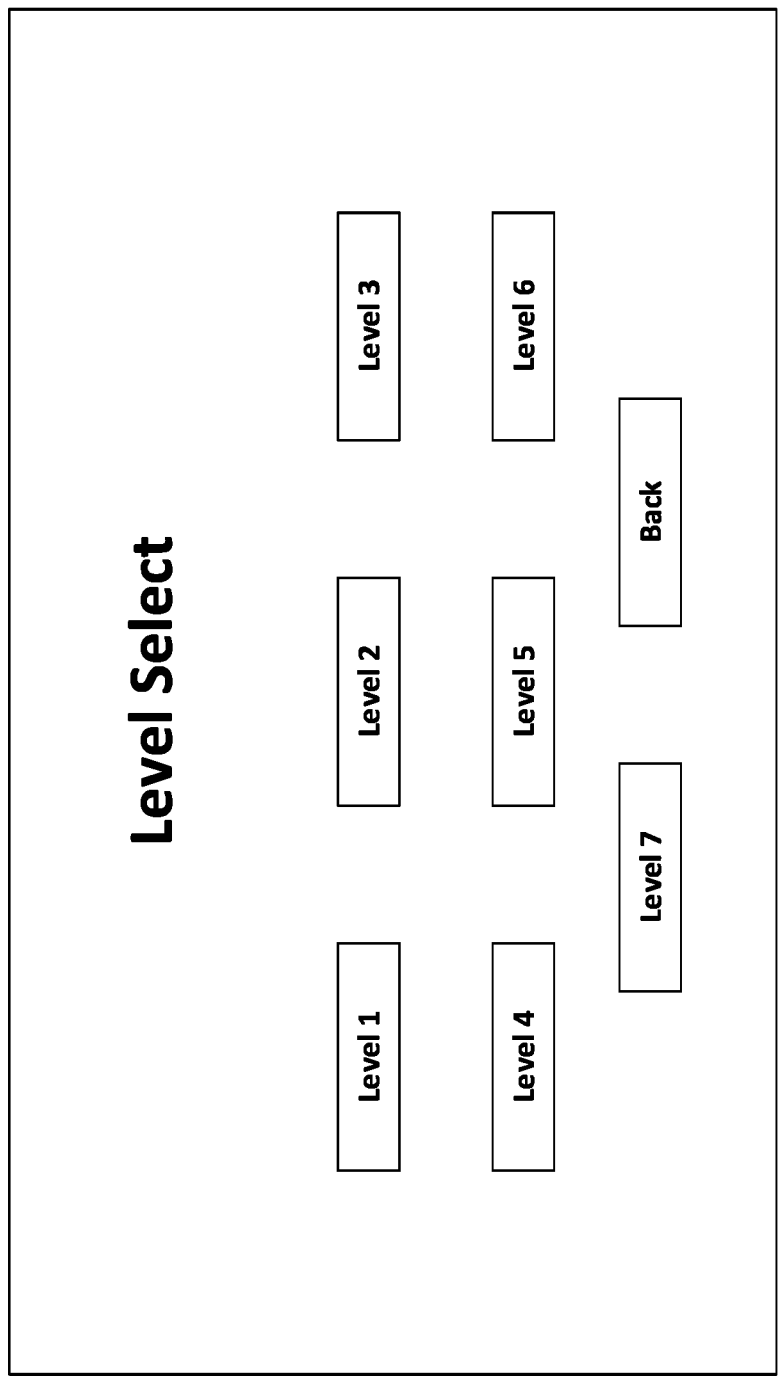
FIG. 8 is select level user interface of the game, in accordance with exemplary embodiments.

When a player clicks on the "Play" button, select level user interface (refer FIG. 8) is shown to the player. The select level user interface offers 7 different game Levels to choose from with option to click back to return to introduction user interface. Levels can be played in any order at any time. However, it is recommender to start at Level 1 and work way up to Level 7.

Figure 9:
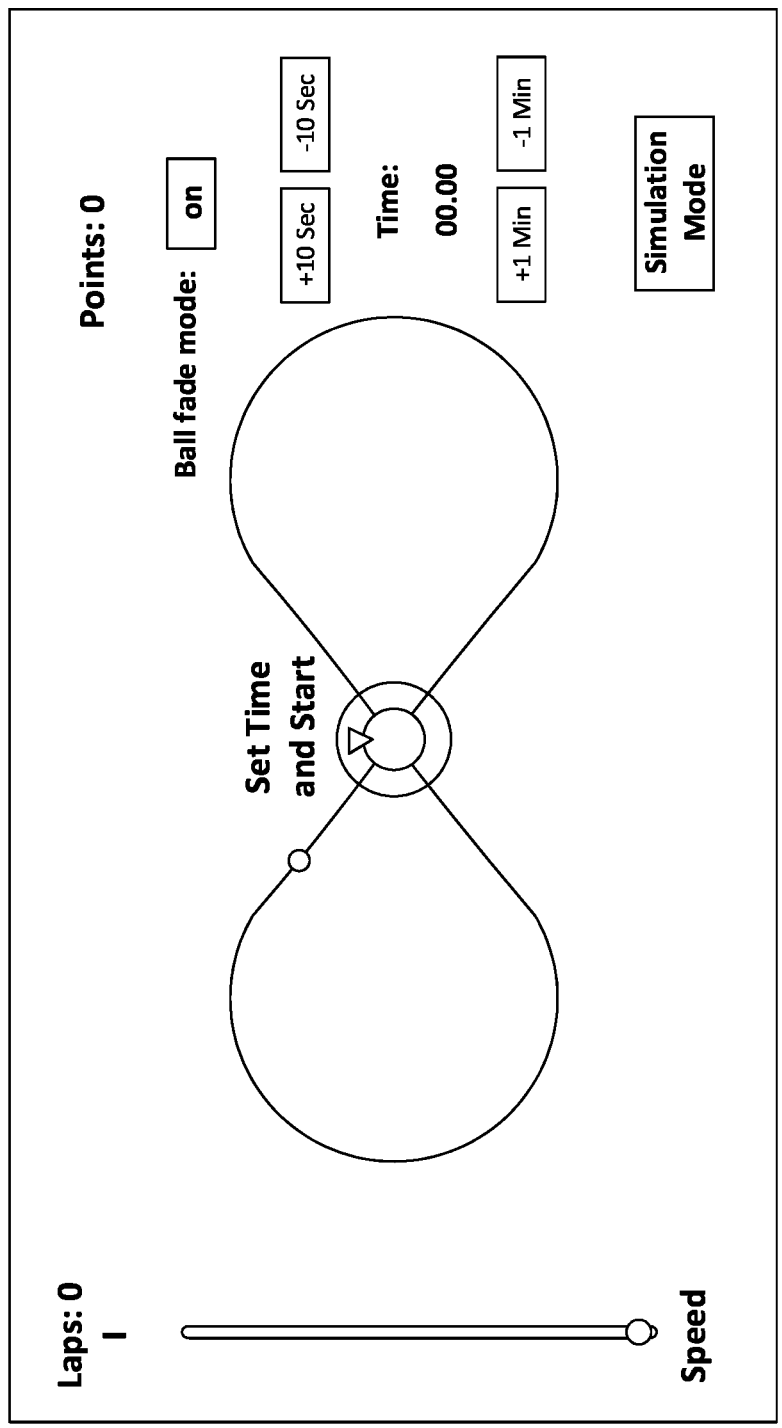
FIG. 9 is Level 1 Game Play user interface of the game, in accordance with exemplary embodiments.

When a player selects Level 1, Level 1 Game Play user interface (refer FIG. 9) is shown to the player. The Level 1 Game Play user interface may have red background. Further, the Level 1 Game Play user interface may show one or more of program time of gameplay, timer, ball fade mode, white ball, points, speed, sound, simulation mode, game over screen. These have been explained in detail below.

Program Time of gameplay—Player must first program allocated time to play and start game. The programing time consist of clicking +10 or −10 Second tabs and +1 or −1 Minute tabs.

Timer—Gameplay timer starts and begins gameplay countdown once player first places cursor over the white ball. The timer counts down from programmed time to zero. When timer reaches zero game automatically ends.

Ball Fade Mode (for blue leading ball)—The blue leading ball is an aid that helps the player follow direction of travel during game play of white ball traveling. Fade mode can be turned on if player wants blue lead ball to fade and disappear after a minute of game play. Fade mode can be turned off if player wants to have blue lead ball on continuously to aid seeing where White ball has to follow.

White Ball—Gameplay starts once player first places cursor over the white ball. It is the focal point of gameplay whereby the player needs to maintain (hover) cursor over the white ball to make it travel around and trace the specific geometric shape to accumulate points and laps over a specific amount of time programmed to play. Gameplay of white ball traveling stops when cursor is not maintained hovering over it. When cursor is re-engaged hovering over the white ball it will then continue to resume travel tracing the geometric shape. (goal is to hover the cursor over white ball for it to continuously maintain travel earning points/ laps.) Whenever white ball is hovered over with cursor it is activated to move in one direction.

Points—Points are accumulated as the player is successfully able to maintain keeping the cursor on the White ball as it travels around the geometric shape for the specific amount of time programmed to play.

Laps (lap Counter)—Counts laps every time white ball successfully makes a full loop from starting point.

Speed—A variable control that determines the speed of travel white ball is moving around (tracing) the geometric pattern while player is maintaining to keep cursor over it. (The greater the player is able to maintain (hover) the cursor over the white ball at higher speeds the greater the number of laps and points accumulate. The less the player is able to maintain (hover) the cursor over the white ball at limiting speeds the lower the number of laps and points accumulate.) Variable speed level ranges from 0.1 to 6. Numeric speed level indicator is located above speed control bar level. Speed control bar level indicates highlighted level speed is set to.

Sound—For Level 1, when player is successfully able to keep cursor over the white ball, then white ball moves to trace around geometric shape with crystal bowl/tuning fork instrument sound sample file frequency of 256 Hz audibly playing simultaneously. Whenever the player is unsuccessful keeping the cursor hovering over the white ball then tracing movement of the white ball stops and crystal bowl instrument sound file frequency of 256 Hz stops audibly playing simultaneously.

Simulation Mode—Player can click on simulation mode option and set amount of time if they want to just watch white ball automatically move/trace along geometric shape and listen to sound frequency without having to physically manipulate hovering cursor over white ball to keep movement in play. Player will be able to receive therapeutic focus benefits by simply watching and listening to the white ball movement along the geometric shape.

Figure 10:
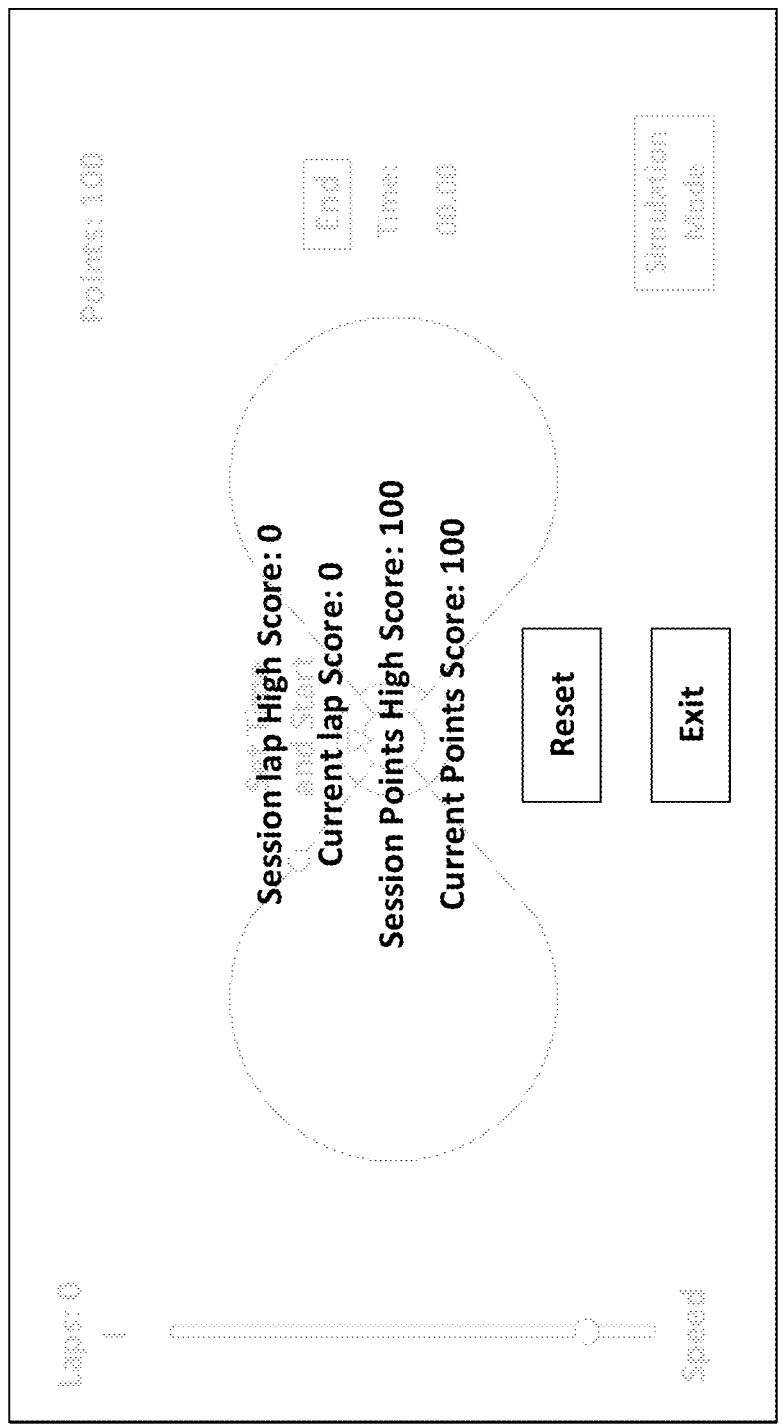
FIG. 10 is Game Over Screen user interface of the game, in accordance with exemplary embodiments.
Figure 11:
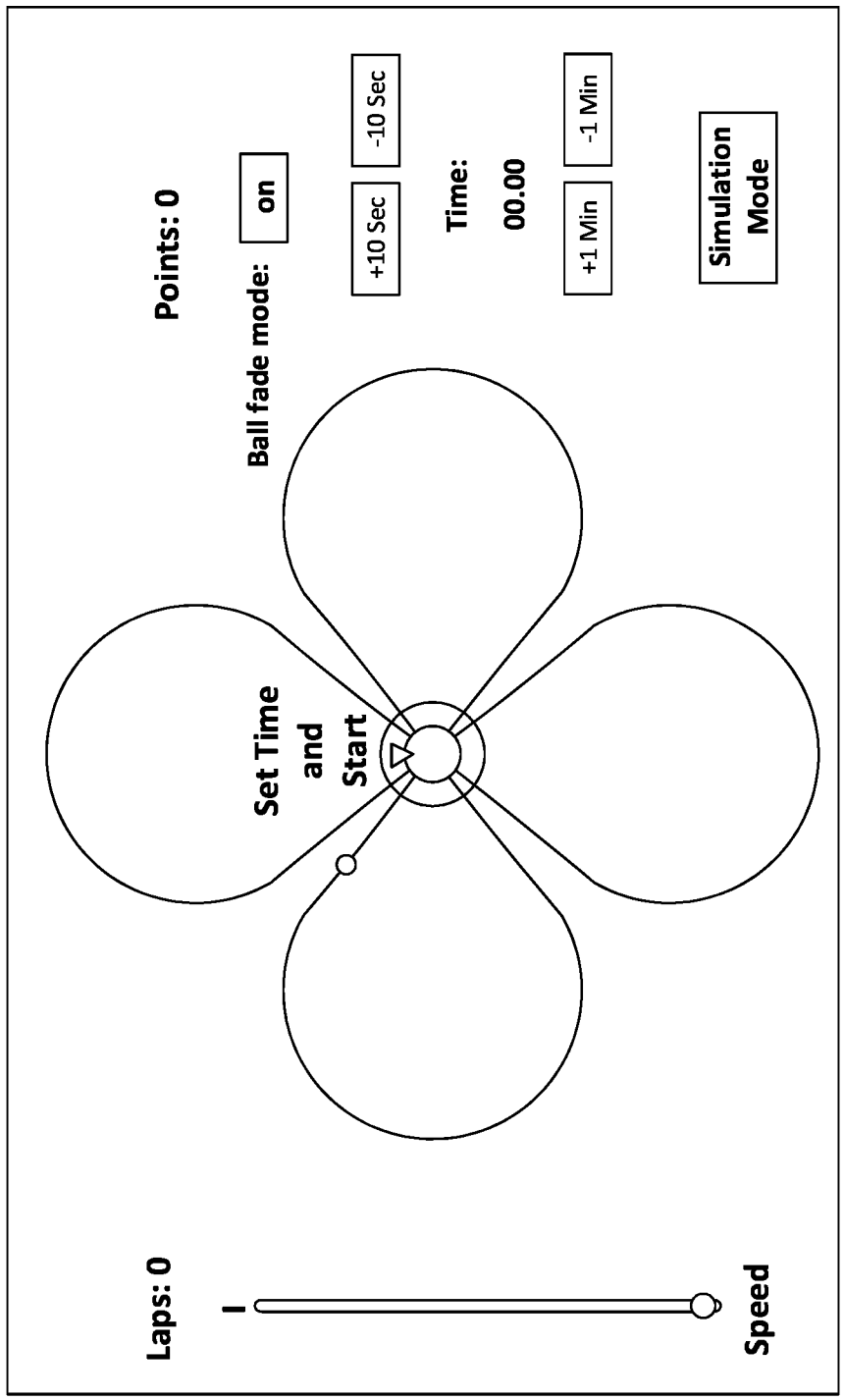
FIG. 11 is Level 2 Game Play user interface of the game, in accordance with exemplary embodiments.

Game Over Screen (refer FIG. 10)—When timer counts down to zero game play ends and screen shows Session Lap High score, Current Lap Score, Session Points High Score for that session, and Current Points Score. Player can click Reset option to restart Level 1 Game or Exit to return to Introduction user interface.

When a player reaches Level 2, Level 2 Game Play user interface (refer FIG. 10) is shown to the player. The Level 2 Game Play user interface may have orange background. Further, the Level 2 Game Play user interface may show one or more of program time of gameplay, timer, ball fade mode, white ball, points, speed, sound, simulation mode, game over screen. These have been explained in detail below.

Program Time of gameplay—Player must first program allocated time to play and start game. Programing time consist of clicking +10 or −10 Second tabs and +1 or −1 Minute tabs Timer—Gameplay timer starts and begins gameplay countdown once player first places cursor over the white ball. The timer counts down from programmed time to zero. When timer reaches zero game automatically ends.

Ball Fade Mode (for blue leading ball)—The blue leading ball is an aid that helps the player follow direction of travel during game play of white ball traveling. Fade mode can be turned on if player wants blue lead ball to fade and disappear after a minute of game play. Fade mode can be turned off if player wants to have blue lead ball on continuously to aid seeing where White ball has to follow.

White Ball—Gameplay starts once player first places cursor over the white ball. It is the focal point of gameplay whereby the player needs to maintain (hover) cursor over the white ball to make it travel around and trace the specific geometric shape to accumulate points and laps over a specific amount of time programmed to play. Gameplay of white ball traveling stops when cursor is not maintained hovering over it. When cursor is re-engaged hovering over the white ball it will then continue to resume travel tracing the geometric shape. (goal is to hover the cursor over white ball for it to continuously maintain travel earning points/laps.) Whenever white ball is hovered over with cursor it is activated to move in one direction.

Points—Points are accumulated as the player is successfully able to maintain keeping the cursor on the White ball as it travels around the geometric shape for the specific amount of time programmed to play.

Laps (lap Counter)—Counts laps every time white ball successfully makes a full loop from starting point.

Speed—A variable control that determines the speed of travel white ball is moving around (tracing) the geometric pattern while player is maintaining to keep cursor over it. (The greater the player is able to maintain (hover) the cursor over the white ball at higher speeds the greater the number of laps and points accumulate. The less the player is able to maintain (hover) the cursor over the white ball at limiting speeds the lower the number of laps and points accumulate.) Variable speed level ranges from 0.1 to 6. Numeric speed level indicator is located above speed control bar level. Speed control bar level indicates highlighted level speed is set to.

Sound—For Level 2, when player is successfully able to keep cursor over the white ball, then white ball moves to trace around geometric shape with crystal bowl/tuning fork instrument sound sample file of 288 Hz audibly playing simultaneously. Whenever the player is unsuccessful keeping the cursor hovering over the white ball then tracing movement of the white ball stops and crystal bowl instrument sound file frequency of 288 Hz stops audibly playing simultaneously.

Simulation Mode—Player can click on simulation mode option and set amount of time if they want to just watch white ball automatically move/trace along geometric shape and listen to sound frequency without having to physically manipulate hovering cursor over white ball to keep movement in play. Player will be able to receive therapeutic focus benefits by simply watching and listening to the white ball movement along the geometric shape.

Figure 12:
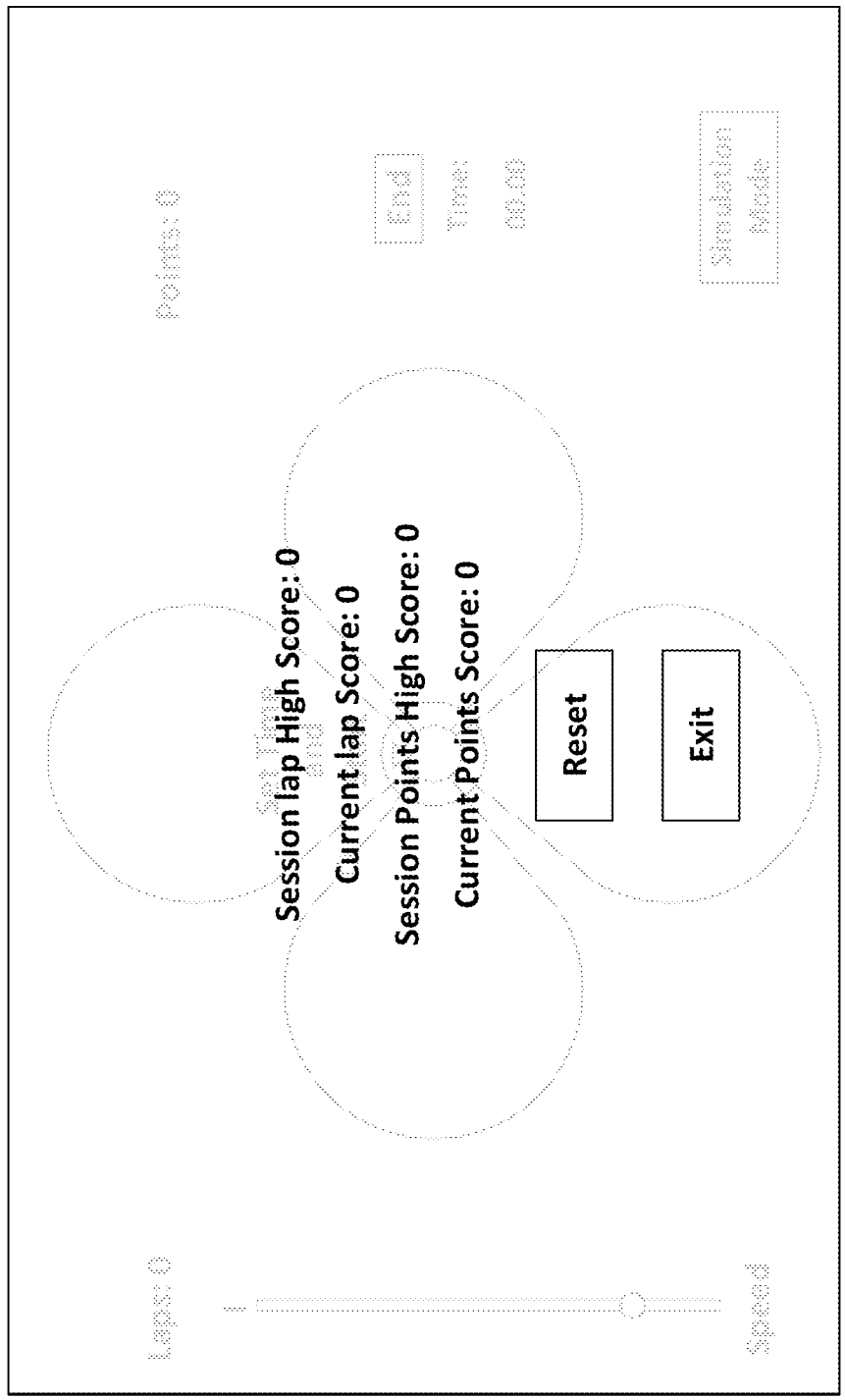
FIG. 12 is Game Over Screen user interface of the game, in accordance with exemplary embodiments.

Game Over Screen (refer FIG. 12)—When timer counts down to zero game play ends and screen shows Session Lap High score, Current Lap Score, Session Points High Score for that session, and Current Points Score. Player can click Reset option to restart Level 2 Game or Exit to return to Introduction user interface.

Figure 13:
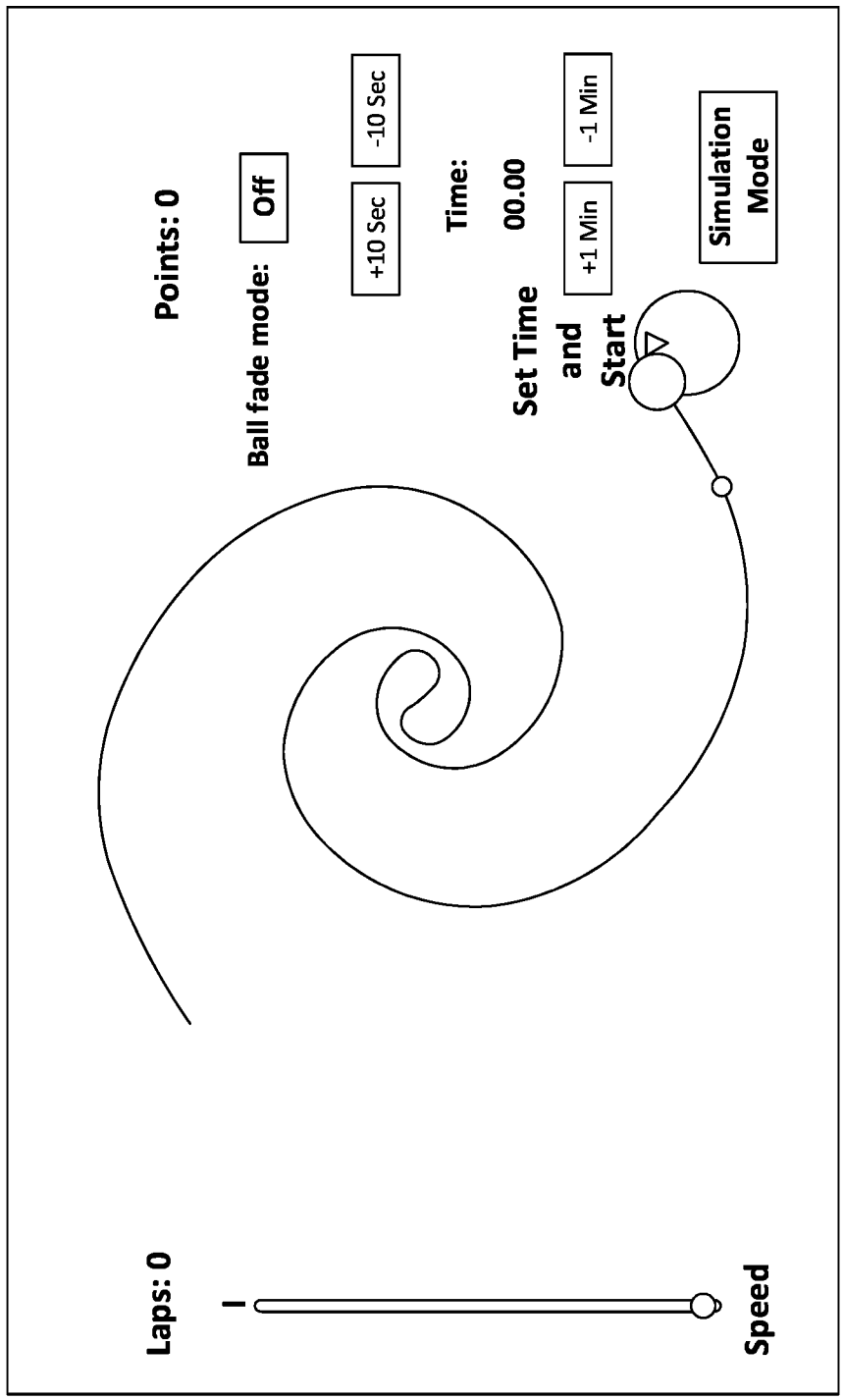
FIG. 13 is Level 3 Game Play user interface of the game, in accordance with exemplary embodiments.

When a player reaches Level 3, Level 3 Game Play user interface (refer FIG. 13) is shown to the player. The Level 3 Game Play user interface may have yellow background. Further, the Level 3 Game Play user interface may show one or more of program time of gameplay, timer, ball fade mode, white ball, points, speed, sound, simulation mode, game over screen. These have been explained in detail below.

Program Time of gameplay—Player must first program allocated time to play and start game. Programing time consist of clicking +10 or −10 Second tabs and +1 or −1 Minute tabs Timer—Gameplay timer starts and begins gameplay countdown once player first places cursor over the white ball. The timer counts down from programmed time to zero. When timer reaches zero game automatically ends.

Ball Fade Mode (for blue leading ball)—The blue leading ball is an aid that helps the player follow direction of travel during game play of white ball traveling. Fade mode can be turned on if player wants blue lead ball to fade and disappear after a minute of game play. Fade mode can be turned off if player wants to have blue lead ball on continuously to aid seeing where White ball has to follow.

White Ball—Gameplay starts once player first places cursor over the white ball. It is the focal point of gameplay whereby the player needs to maintain (hover) cursor over the white ball to make it travel around and trace the specific geometric shape to accumulate points and laps over a specific amount of time programmed to play. Gameplay of white ball traveling stops when cursor is not maintained hovering over it. When cursor is re-engaged hovering over the white ball it will then continue to resume travel tracing the geometric shape. (goal is to hover the cursor over white ball for it to continuously maintain travel earning points/laps.) Whenever white ball is hovered over with cursor it is activated to move in one direction.

Points—Points are accumulated as the player is successfully able to maintain keeping the cursor on the White ball as it travels around the geometric shape for the specific amount of time programmed to play.

Laps (lap Counter)—Counts laps every time white ball successfully makes a full loop from starting point.

Speed—A variable control that determines the speed of travel white ball is moving around (tracing) the geometric pattern while player is maintaining to keep cursor over it. (The greater the player is able to maintain (hover) the cursor over the white ball at higher speeds the greater the number of laps and points accumulate. The less the player is able to maintain (hover) the cursor over the white ball at limiting speeds the lower the number of laps and points accumulate.) Variable speed level ranges from 0.1 to 6. Numeric speed level indicator is located above speed control bar level. Speed control bar level indicates highlighted level speed is set to.

Sound—For Level 3, when player is successfully able to keep cursor over the white ball, then white ball moves to trace around geometric shape with crystal bowl/tuning fork instrument sound sample file of 323 Hz audibly playing simultaneously. Whenever the player is unsuccessful keeping the cursor hovering over the white ball then tracing movement of the white ball stops and crystal bowl instrument sound file frequency of 323 Hz stops audibly playing simultaneously.

Simulation Mode—Player can click on simulation mode option and set amount of time if they want to just watch white ball automatically move/trace along geometric shape and listen to sound frequency without having to physically manipulate hovering cursor over white ball to keep movement in play. Player will be able to receive therapeutic focus benefits by simply watching and listening to the white ball movement along the geometric shape.

Figure 14:
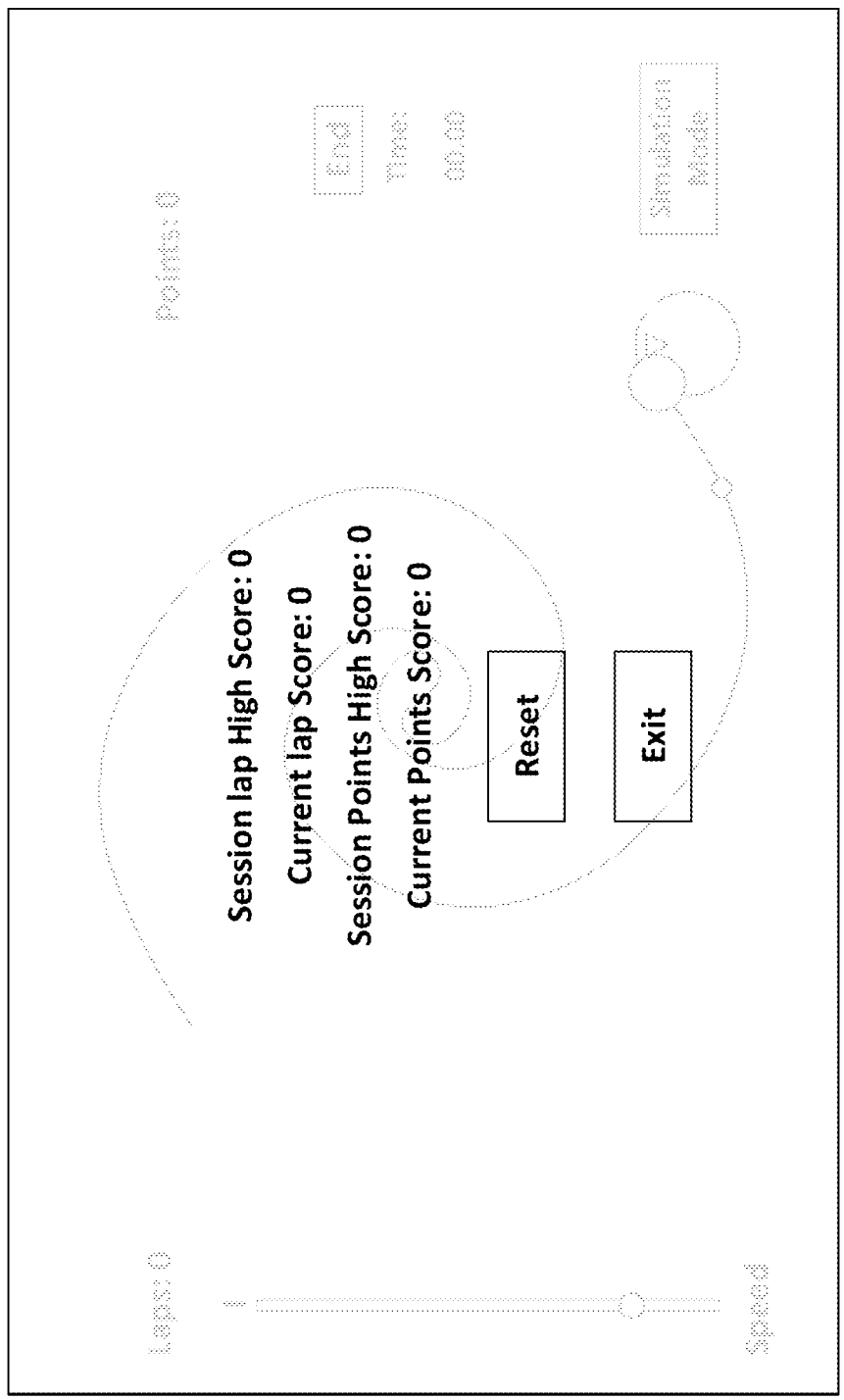
FIG. 14 is Game Over Screen user interface of the game, in accordance with exemplary embodiments.

Game Over Screen (refer FIG. 14)—When timer counts down to zero game play ends and screen shows Session Lap High score, Current Lap Score, Session Points High Score for that session, and Current Points Score. Player can click Reset option to restart Level 3 Game or Exit to return to Introduction user interface.

Figure 15:
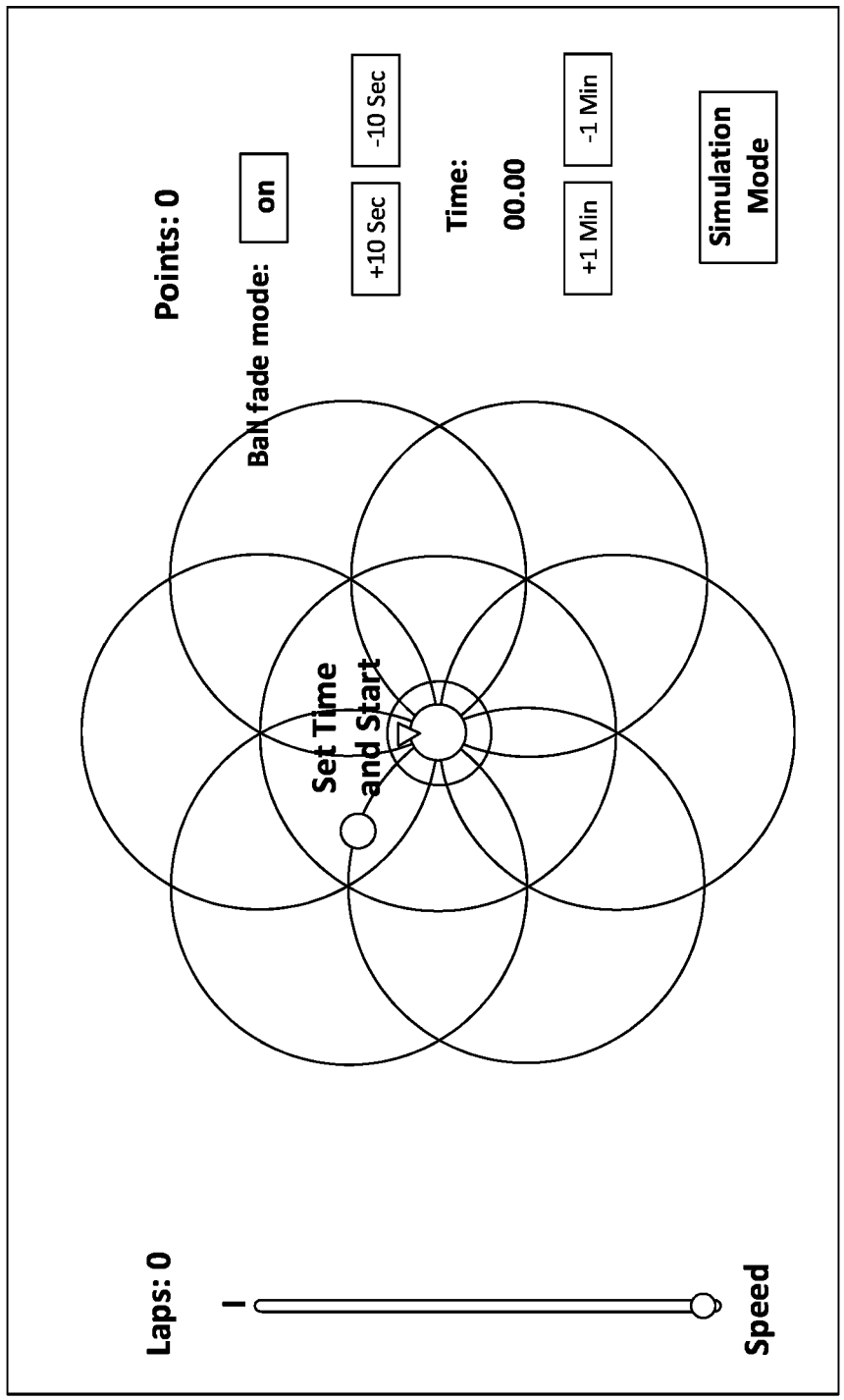
FIG. 15 is Level 4 Game Play user interface of the game, in accordance with exemplary embodiments.

When a player reaches Level 4, Level 4 Game Play user interface (refer FIG. 15) is shown to the player. The Level 4 Game Play user interface may have green background. Further, the Level 4 Game Play user interface may show one or more of program time of gameplay, timer, ball fade mode, white ball, points, speed, sound, simulation mode, game over screen. These have been explained in detail below.

Program Time of gameplay—Player must first program allocated time to play and start game. Programing time consist of clicking +10 or −10 Second tabs and +1 or −1 Minute tabs.

Timer—Gameplay timer starts and begins gameplay countdown once player first places cursor over the white ball. The timer counts down from programmed time to zero. When timer reaches zero game automatically ends.

Ball Fade Mode (for blue leading ball)—The blue leading ball is an aid that helps the player follow direction of travel during game play of white ball traveling. Fade mode can be turned on if player wants blue lead ball to fade and disappear after a minute of game play. Fade mode can be turned off if player wants to have blue lead ball on continuously to aid seeing where White ball has to follow.

White Ball—Gameplay starts once player first places cursor over the white ball. It is the focal point of gameplay whereby the player needs to maintain (hover) cursor over the white ball to make it travel around and trace the specific geometric shape to accumulate points and laps over a specific amount of time programmed to play. Gameplay of white ball traveling stops when cursor is not maintained hovering over it. When cursor is re-engaged hovering over the white ball it will then continue to resume travel tracing the geometric shape. (goal is to hover the cursor over white ball for it to continuously maintain travel earning points/laps.) Whenever white ball is hovered over with cursor it is activated to move in one direction.

Points—Points are accumulated as the player is successfully able to maintain keeping the cursor on the White ball as it travels around the geometric shape for the specific amount of time programmed to play.

Laps (lap Counter)—Counts laps every time white ball successfully makes a full loop from starting point.

Speed—A variable control that determines the speed of travel white ball is moving around (tracing) the geometric pattern while player is maintaining to keep cursor over it. (The greater the player is able to maintain (hover) the cursor over the white ball at higher speeds the greater the number of laps and points accumulate. The less the player is able to maintain (hover) the cursor over the white ball at limiting speeds the lower the number of laps and points accumulate.) Variable speed level ranges from 0.1 to 6. Numeric speed level indicator is located above speed control bar level. Speed control bar level indicates highlighted level speed is set to.

Sound—For Level 4, when player is successfully able to keep cursor over the white ball, then white ball moves to trace around geometric shape with crystal bowl/tuning fork instrument sound sample file of 343 Hz audibly playing simultaneously. Whenever the player is unsuccessful keeping the cursor hovering over the white ball then tracing movement of the white ball stops and crystal bowl instrument sound file frequency of 343 Hz stops audibly playing simultaneously.

Simulation Mode—Player can click on simulation mode option and set amount of time if they want to just watch white ball automatically move/trace along geometric shape and listen to sound frequency without having to physically manipulate hovering cursor over white ball to keep movement in play. Player will be able to receive therapeutic focus benefits by simply watching and listening to the white ball movement along the geometric shape.

Figure 16:
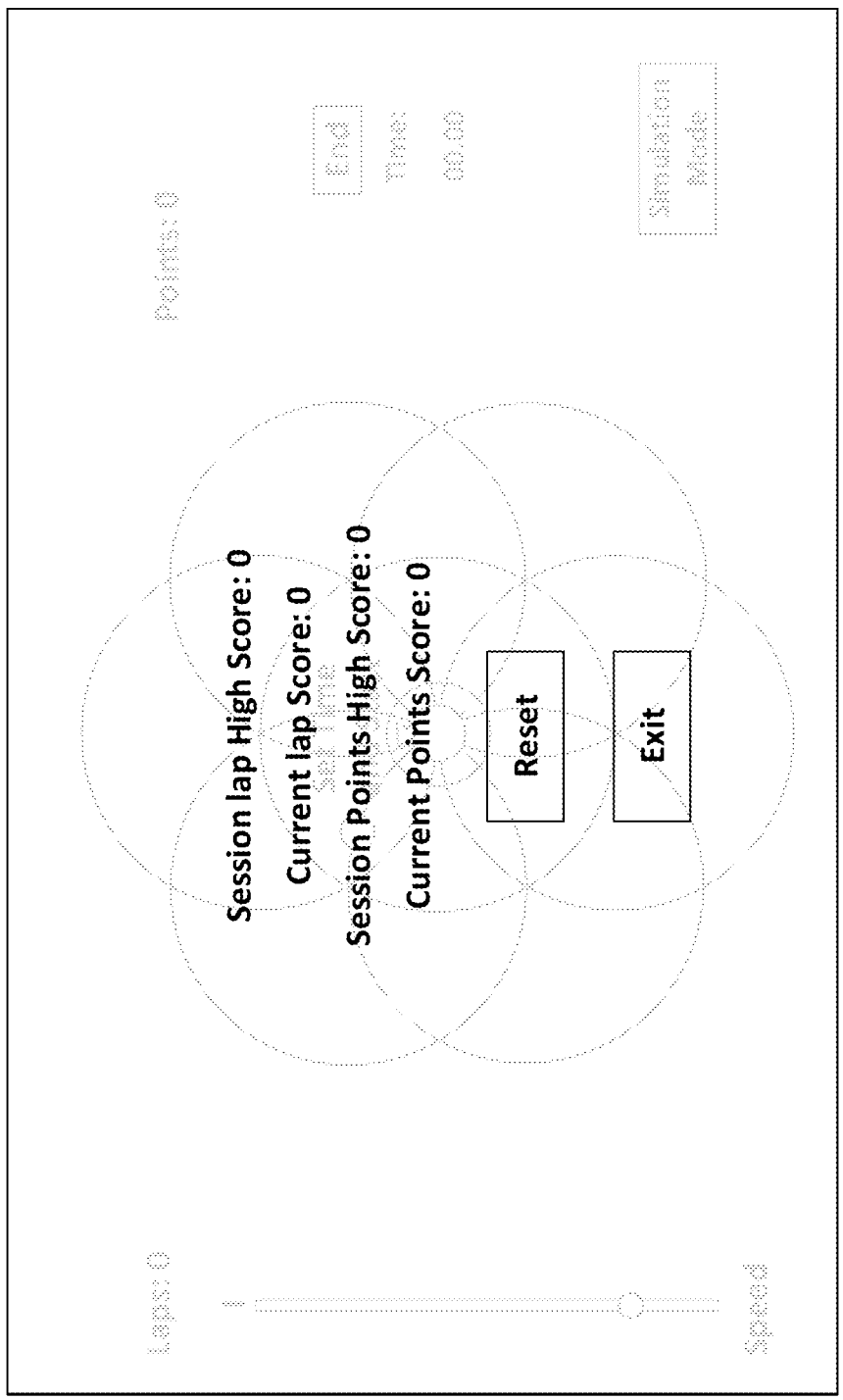
FIG. 16 is Game Over Screen user interface of the game, in accordance with exemplary embodiments.

Game Over Screen (refer FIG. 16)—When timer counts down to zero game play ends and screen shows Session Lap High score, Current Lap Score, Session Points High Score for that session, and Current Points Score. Player can click Reset option to restart Level 4 Game or Exit to return to Introduction user interface.

Figure 17:
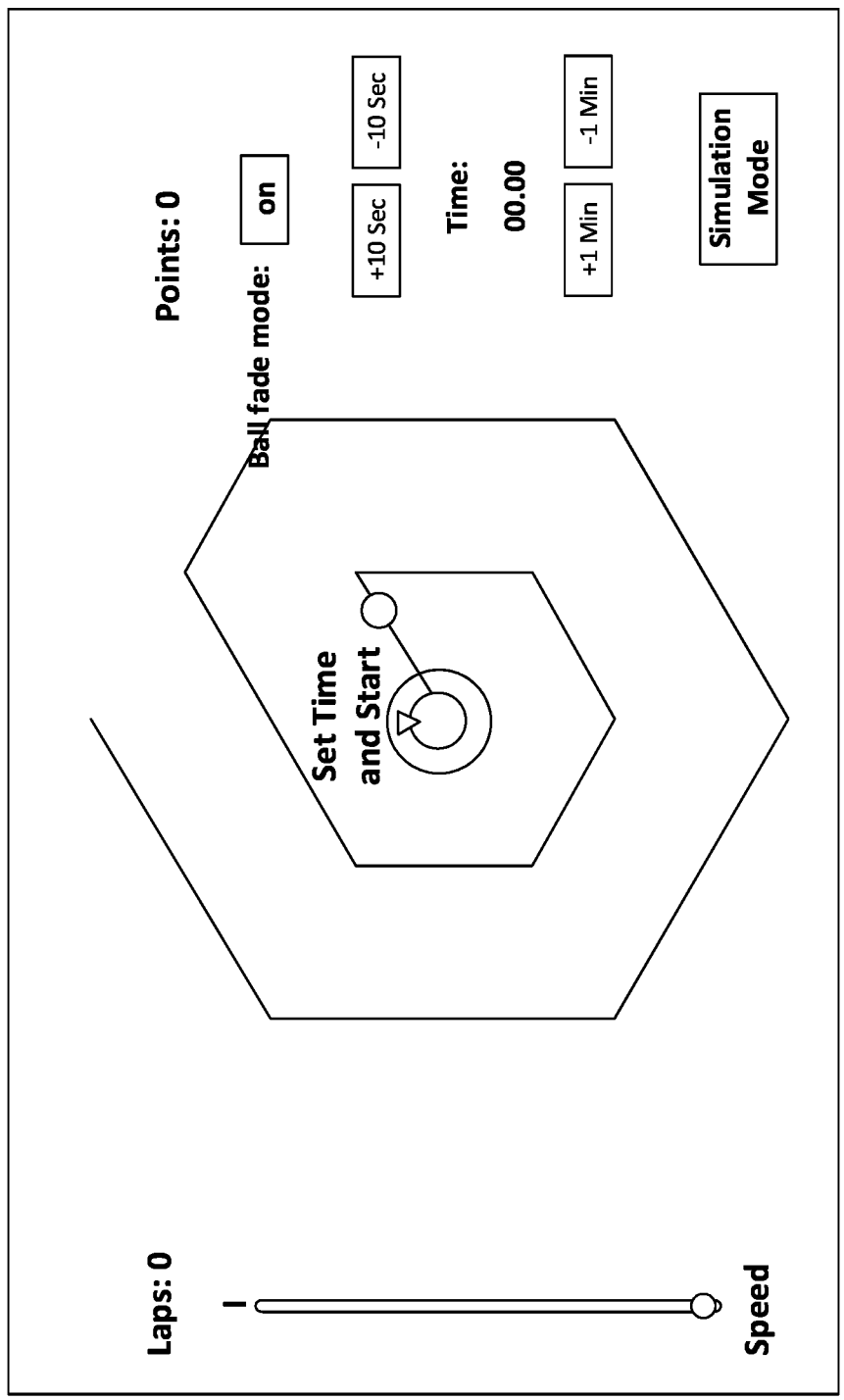
FIG. 17 is Level 5 Game Play user interface of the game, in accordance with exemplary embodiments.

When a player reaches Level 5, Level 5 Game Play user interface (refer FIG. 17) is shown to the player. The Level 5 Game Play user interface may have light blue background. Further, the Level 5 Game Play user interface may show one or more of program time of gameplay, timer, ball fade mode, white ball, points, speed, sound, simulation mode, game over screen. These have been explained in detail below.

Program Time of gameplay—Player must first program allocated time to play and start game. Programing time consist of clicking +10 or −10 Second tabs and +1 or −1 Minute tabs.

Timer—Gameplay timer starts and begins gameplay countdown once player first places cursor over the white ball. The timer counts down from programmed time to zero. When timer reaches zero game automatically ends.

Ball Fade Mode (for blue leading ball)—The blue leading ball is an aid that helps the player follow direction of travel during game play of white ball traveling. Fade mode can be turned on if player wants blue lead ball to fade and disappear after a minute of game play. Fade mode can be turned off if player wants to have blue lead ball on continuously to aid seeing where White ball has to follow.

White Ball—Gameplay starts once player first places cursor over the white ball. It is the focal point of gameplay whereby the player needs to maintain (hover) cursor over the white ball to make it travel around and trace the specific geometric shape to accumulate points and laps over a specific amount of time programmed to play. Gameplay of white ball traveling stops when cursor is not maintained hovering over it. When cursor is re-engaged hovering over the white ball it will then continue to resume travel tracing the geometric shape. (goal is to hover the cursor over white ball for it to continuously maintain travel earning points/laps.) Whenever white ball is hovered over with cursor it is activated to move in one direction.

Points—Points are accumulated as the player is successfully able to maintain keeping the cursor on the White ball as it travels around the geometric shape for the specific amount of time programmed to play.

Laps (lap Counter)—Counts laps every time white ball successfully makes a full loop from starting point.

Speed—A variable control that determines the speed of travel white ball is moving around (tracing) the geometric pattern while player is maintaining to keep cursor over it. (The greater the player is able to maintain (hover) the cursor over the white ball at higher speeds the greater the number of laps and points accumulate. The less the player is able to maintain (hover) the cursor over the white ball at limiting speeds the lower the number of laps and points accumulate.) Variable speed level ranges from 0.1 to 6. Numeric speed level indicator is located above speed control bar level. Speed control bar level indicates highlighted level speed is set to.

Sound—For Level 5, when player is successfully able to keep cursor over the white ball, then white ball moves to trace around geometric shape with crystal bowl/tuning fork instrument sound sample file of 385 Hz audibly playing simultaneously. Whenever the player is unsuccessful keeping the cursor hovering over the white ball then tracing movement of the white ball stops and crystal bowl instrument sound file frequency of 385 Hz stops audibly playing simultaneously.

Simulation Mode—Player can click on simulation mode option and set amount of time if they want to just watch white ball automatically move/trace along geometric shape and listen to sound frequency without having to physically manipulate hovering cursor over white ball to keep movement in play. Player will be able to receive therapeutic focus benefits by simply watching and listening to the white ball movement along the geometric shape.

Figure 18:
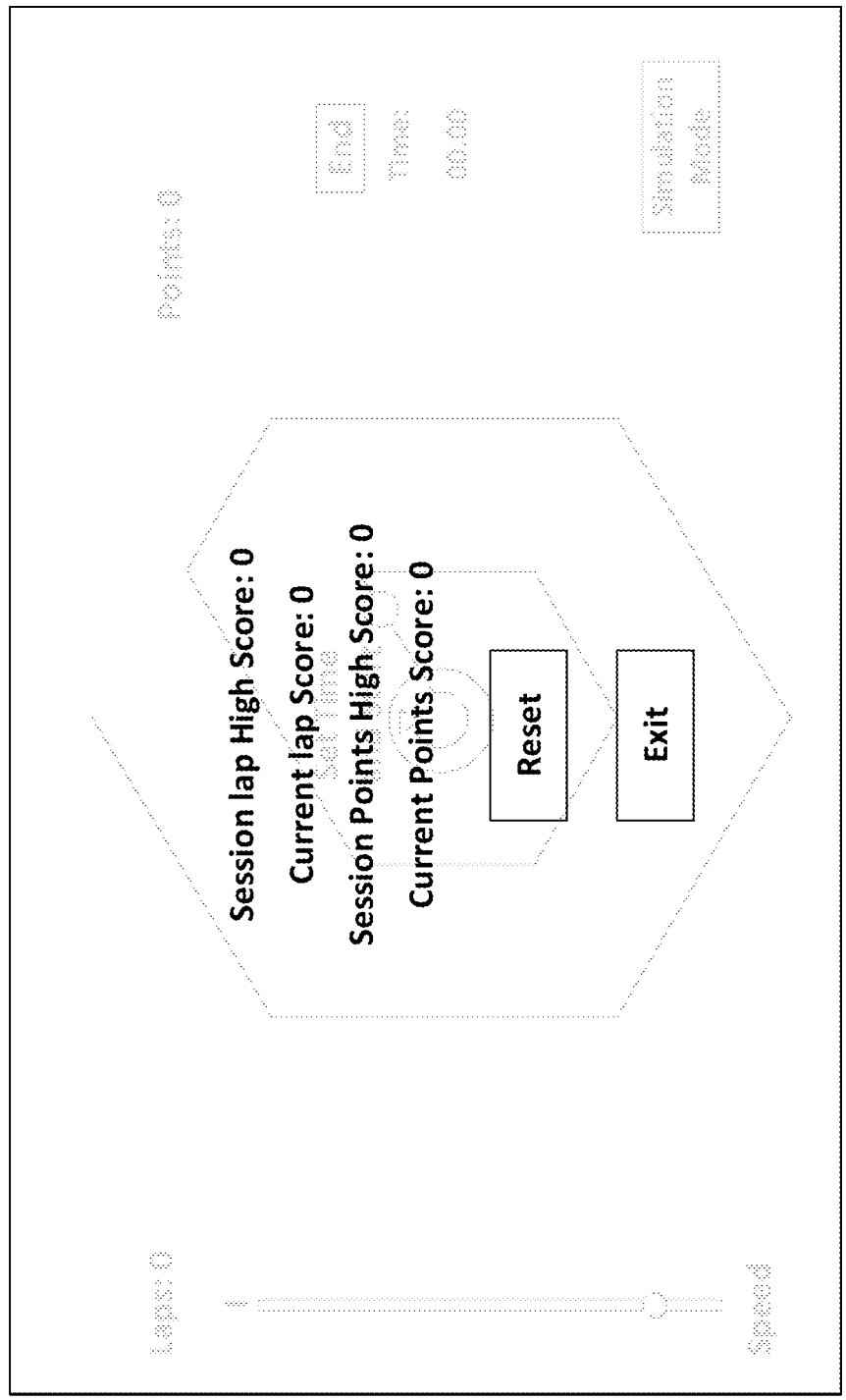
FIG. 18 is Game Over Screen user interface of the game, in accordance with exemplary embodiments.

Game Over Screen (refer FIG. 18)—When timer counts down to zero game play ends and screen shows Session Lap High score, Current Lap Score, Session Points High Score for that session, and Current Points Score. Player can click Reset option to restart Level 5 Game or Exit to return to Introduction user interface.

Figure 19:
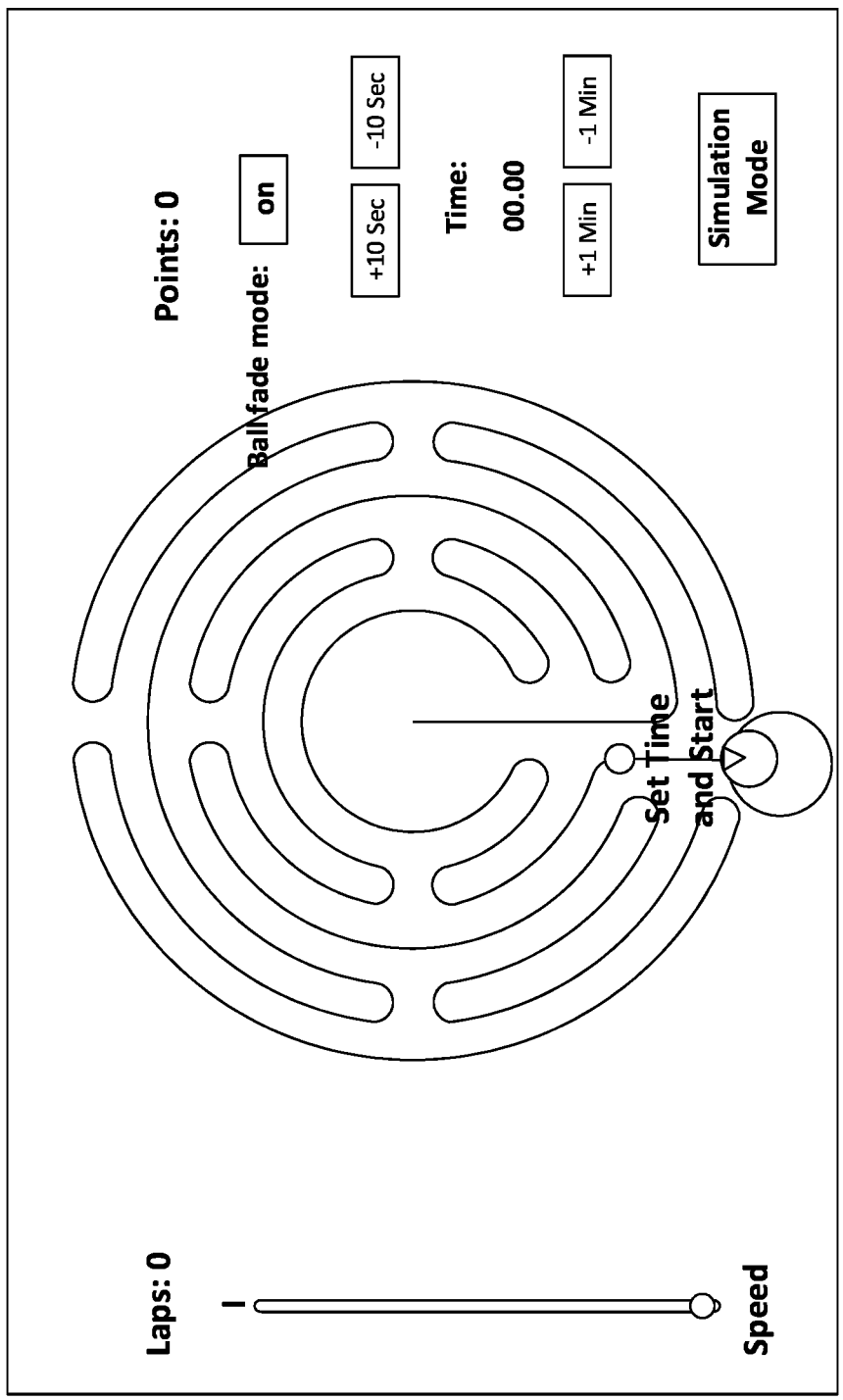
FIG. 19 is Level 6 Game Play user interface of the game, in accordance with exemplary embodiments.

When a player reaches Level 6, Level 6 Game Play user interface (refer FIG. 19) is shown to the player. The Level 6 Game Play user interface may have indigo blue background. Further, the Level 6 Game Play user interface may show one or more of program time of gameplay, timer, ball fade mode, white ball, points, speed, sound, simulation mode, game over screen. These have been explained in detail below.

Program Time of gameplay—Player must first program allocated time to play and start game. Programing time consist of clicking +10 or −10 Second tabs and +1 or −1 Minute tabs Timer—Gameplay timer starts and begins gameplay countdown once player first places cursor over the white ball. The timer counts down from programmed time to zero. When timer reaches zero game automatically ends.

Ball Fade Mode (for blue leading ball)—The blue leading ball is an aid that helps the player follow direction of travel during game play of white ball traveling. Fade mode can be turned on if player wants blue lead ball to fade and disappear after a minute of game play. Fade mode can be turned off if player wants to have blue lead ball on continuously to aid seeing where White ball has to follow.

White Ball—Gameplay starts once player first places cursor over the white ball. It is the focal point of gameplay whereby the player needs to maintain (hover) cursor over the white ball to make it travel around and trace the specific geometric shape to accumulate points and laps over a specific amount of time programmed to play. Gameplay of white ball traveling stops when cursor is not maintained hovering over it. When cursor is re-engaged hovering over the white ball it will then continue to resume travel tracing the geometric shape. (goal is to hover the cursor over white ball for it to continuously maintain travel earning points/laps.) Whenever white ball is hovered over with cursor it is activated to move in one direction.

Points—Points are accumulated as the player is successfully able to maintain keeping the cursor on the White ball as it travels around the geometric shape for the specific amount of time programmed to play.

Laps (lap Counter)—Counts laps every time white ball successfully makes a full loop from starting point.

Speed—A variable control that determines the speed of travel white ball is moving around (tracing) the geometric pattern while player is maintaining to keep cursor over it. (The greater the player is able to maintain (hover) the cursor over the white ball at higher speeds the greater the number of laps and points accumulate. The less the player is able to maintain (hover) the cursor over the white ball at limiting speeds the lower the number of laps and points accumulate.) Variable speed level ranges from 0.1 to 6. Numeric speed level indicator is located above speed control bar level. Speed control bar level indicates highlighted level speed is set to.

Sound—For Level 6, when player is successfully able to keep cursor over the white ball, then white ball moves to trace around geometric shape with crystal bowl/tuning fork instrument sound sample file of 432 Hz audibly playing simultaneously. Whenever the player is unsuccessful keeping the cursor hovering over the white ball then tracing movement of the white ball stops and crystal bowl instrument sound file frequency of 432 Hz stops audibly playing simultaneously.

Simulation Mode—Player can click on simulation mode option and set amount of time if they want to just watch white ball automatically move/trace along geometric shape and listen to sound frequency without having to physically manipulate hovering cursor over white ball to keep movement in play. Player will be able to receive therapeutic focus benefits by simply watching and listening to the white ball movement along the geometric shape.

Figure 20:
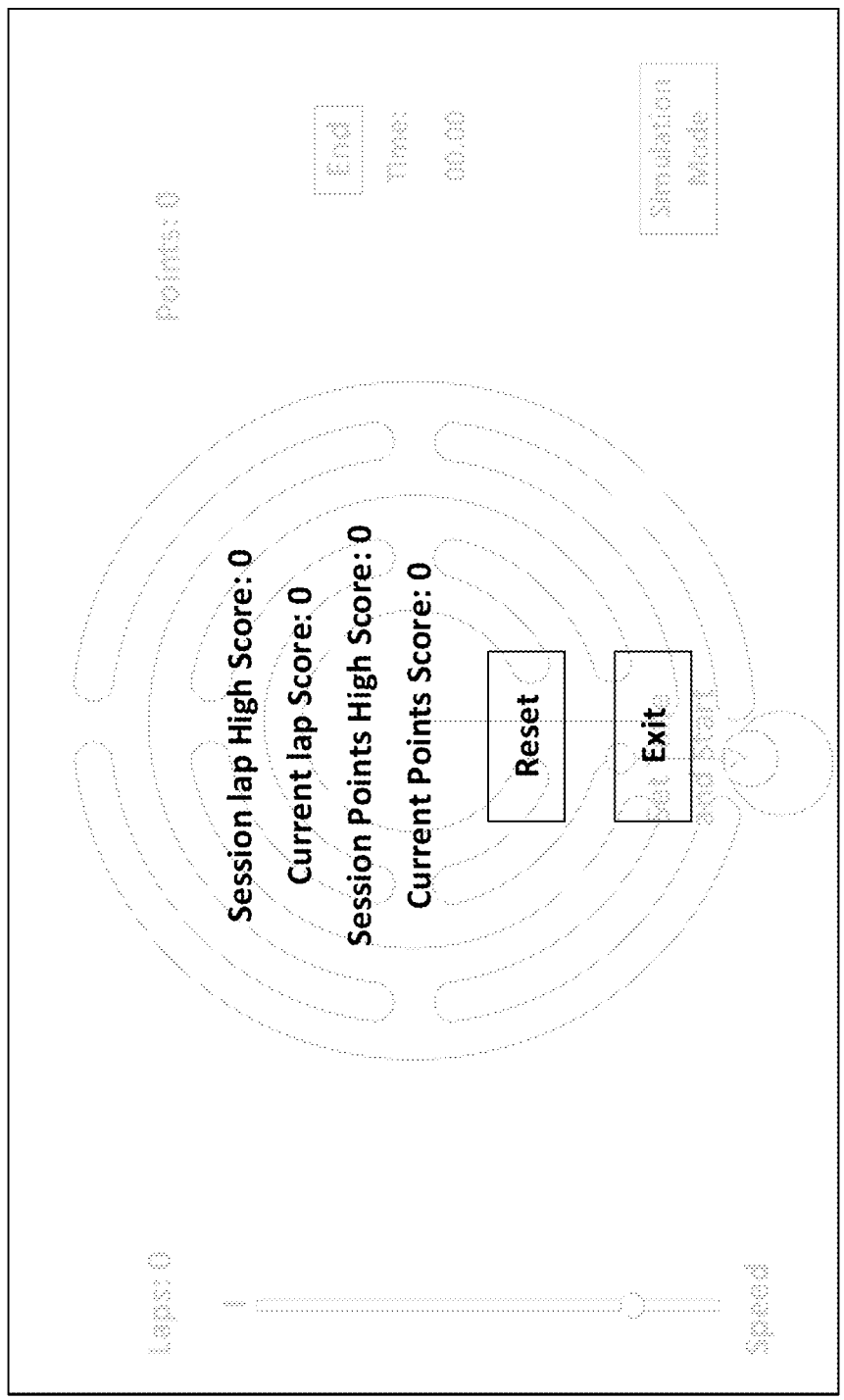
FIG. 20 is Game Over Screen user interface of the game, in accordance with exemplary embodiments.

Game Over Screen (refer FIG. 20)—When timer counts down to zero game play ends and screen shows Session Lap High score, Current Lap Score, Session Points High Score for that session, and Current Points Score. Player can click Reset option to restart Level 6 Game or Exit to return to Introduction user interface.

Figure 21:
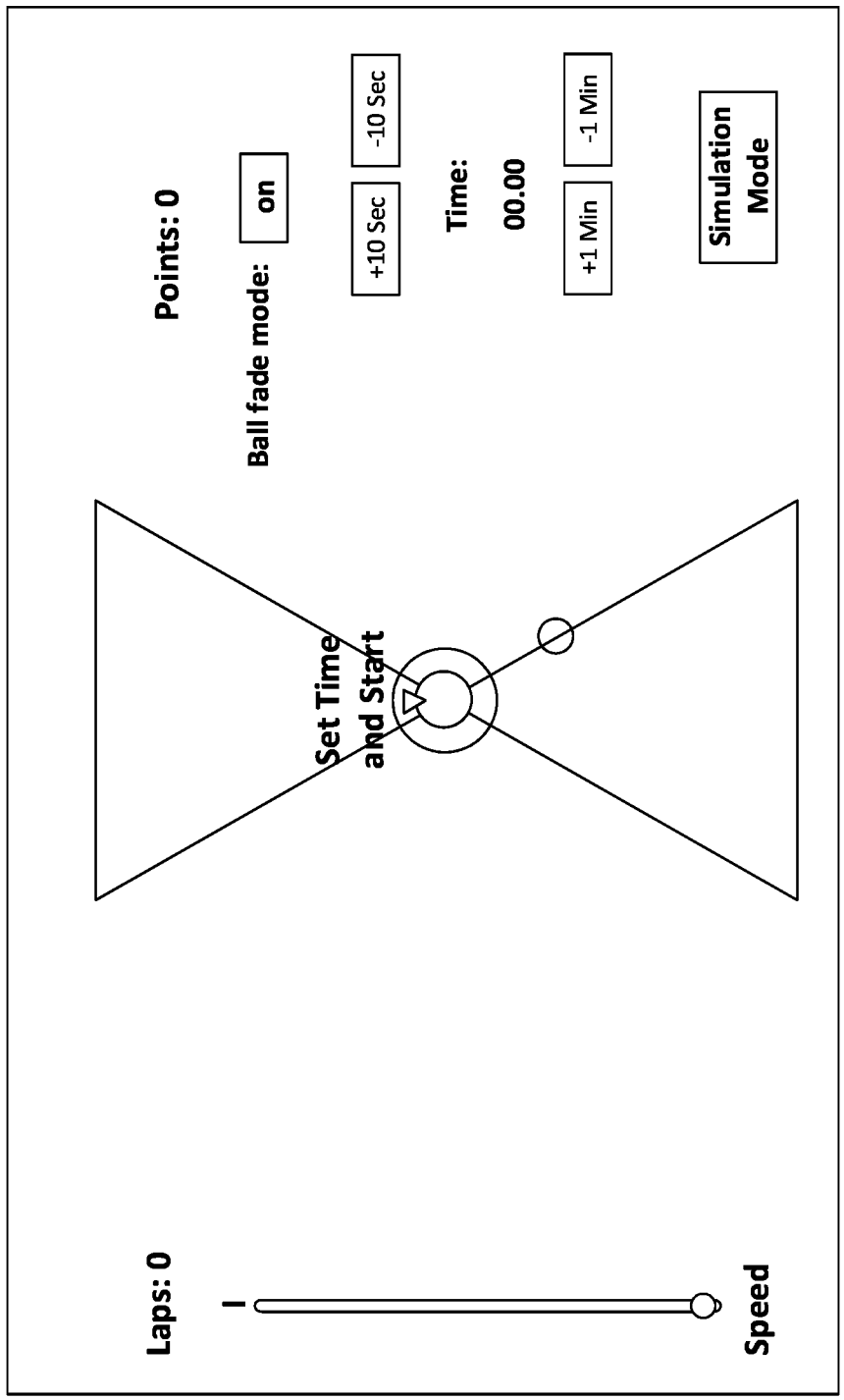
FIG. 21 is Level 7 Game Play user interface of the game, in accordance with exemplary embodiments.

When a player reaches Level 7, Level 7 Game Play user interface (refer FIG. 21) is shown to the player. The Level 7 Game Play user interface may have violet background. Further, the Level 7 Game Play user interface may show one or more of program time of gameplay, timer, ball fade mode, white ball, points, speed, sound, simulation mode, game over screen. These have been explained in detail below.

Program Time of gameplay—Player must first program allocated time to play and start game. Programing time consist of clicking +10 or −10 Second tabs and +1 or −1 Minute tabs.

Timer—Gameplay timer starts and begins gameplay countdown once player first places cursor over the white ball. The timer counts down from programmed time to zero. When timer reaches zero game automatically ends.

Ball Fade Mode (for blue leading ball)—The blue leading ball is an aid that helps the player follow direction of travel during game play of white ball traveling. Fade mode can be turned on if player wants blue lead ball to fade and disappear after a minute of game play. Fade mode can be turned off if player wants to have blue lead ball on continuously to aid seeing where White ball has to follow.

White Ball—Gameplay starts once player first places cursor over the white ball. It is the focal point of gameplay whereby the player needs to maintain (hover) cursor over the white ball to make it travel around and trace the specific geometric shape to accumulate points and laps over a specific amount of time programmed to play. Gameplay of white ball traveling stops when cursor is not maintained hovering over it. When cursor is re-engaged hovering over the white ball it will then continue to resume travel tracing the geometric shape. (goal is to hover the cursor over white ball for it to continuously maintain travel earning points/laps.) Whenever white ball is hovered over with cursor it is activated to move in one direction.

Points—Points are accumulated as the player is successfully able to maintain keeping the cursor on the White ball as it travels around the geometric shape for the specific amount of time programmed to play.

Laps (lap Counter)—Counts laps every time white ball successfully makes a full loop from starting point.

Speed—A variable control that determines the speed of travel white ball is moving around (tracing) the geometric pattern while player is maintaining to keep cursor over it. (The greater the player is able to maintain (hover) the cursor over the white ball at higher speeds the greater the number of laps and points accumulate. The less the player is able to maintain (hover) the cursor over the white ball at limiting speeds the lower the number of laps and points accumulate.) Variable speed level ranges from 0.1 to 6. Numeric speed level indicator is located above speed control bar level. Speed control bar level indicates highlighted level speed is set to.

Sound—For Level 7, when player is successfully able to keep cursor over the white ball, then white ball moves to trace around geometric shape with crystal bowl/tuning fork instrument sound sample file of 484 Hz audibly playing simultaneously. Whenever the player is unsuccessful keeping the cursor hovering over the white ball then tracing movement of the white ball stops and crystal bowl instrument sound file frequency of 484 Hz stops audibly playing simultaneously.

Simulation Mode—Player can click on simulation mode option and set amount of time if they want to just watch white ball automatically move/trace along geometric shape and listen to sound frequency without having to physically manipulate hovering cursor over white ball to keep movement in play. Player will be able to receive therapeutic focus benefits by simply watching and listening to the white ball movement along the geometric shape.

Figure 22:
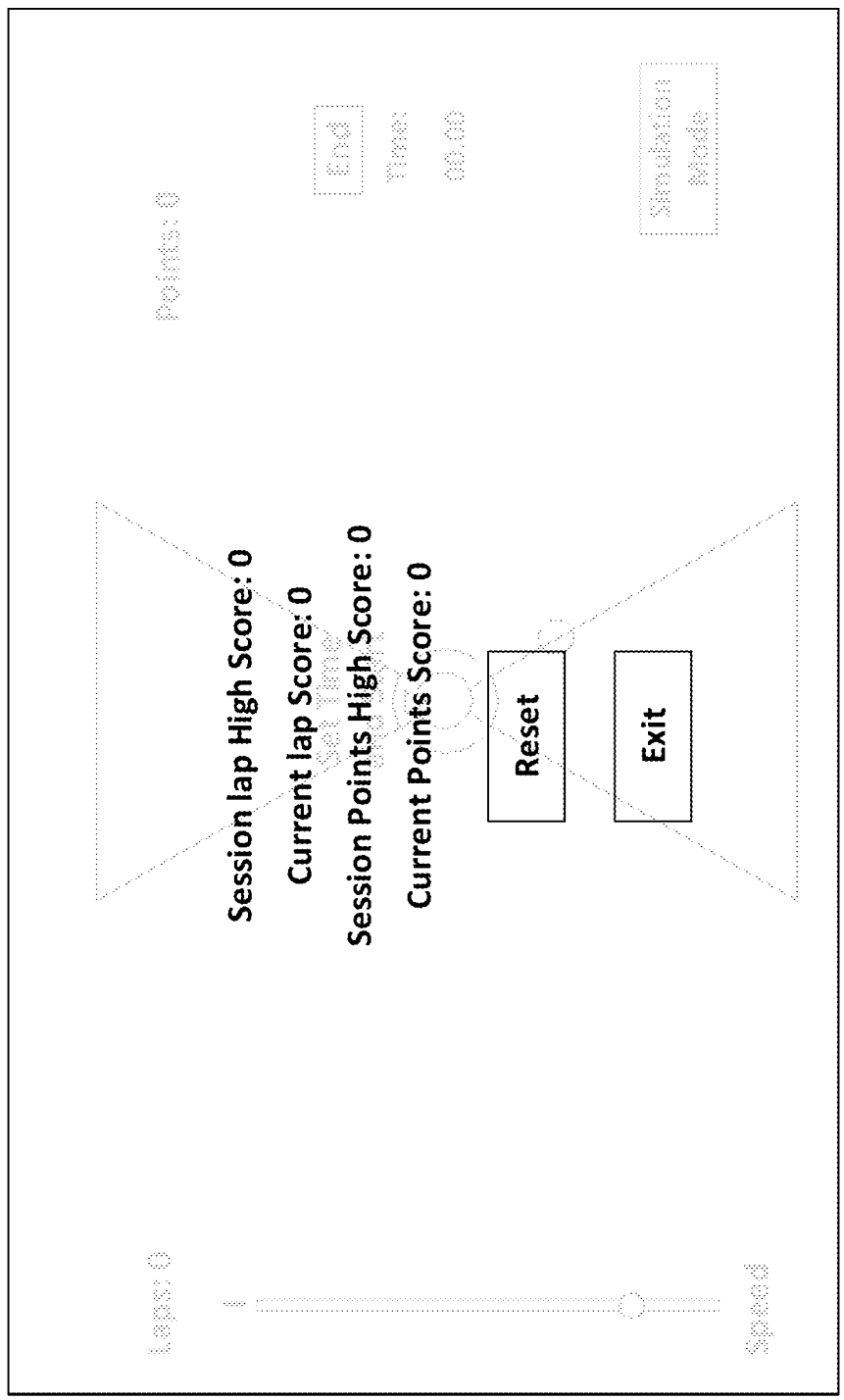
FIG. 22 is Game Over Screen user interface of the game, in accordance with exemplary embodiments.

Game Over Screen (refer FIG. 22)—When timer counts down to zero game play ends and screen shows Session Lap High score, Current Lap Score, Session Points High Score for that session, and Current Points Score. Player can click Reset option to restart Level 7 Game or Exit to return to Introduction user interface.

On the introduction user interface, when a player clicks on the "Instructions" button, instruction user interface (refer FIG. 23) is shown to the player. The instruction user interface shows game instructions for player.

On the introduction user interface, when a player clicks on the "Credits" button, credits user interface (refer FIG. 24) is shown to the player. The credits user interface shows contact information of the game developer and owner of Infinity Lightpath.

On the introduction user interface, when a player clicks on the "Exit" button, the game exits and returns to desktop.

In accordance with some embodiments, the other extensions that may be needed to run the Infinity Lightpath software for the Mac may include Apple Magic Trackpad 2-Trackpad-Bluetooth 4.0-Silver Mfg. Part: MJ2R2LL/A|CDW Part: 3868764|UNSPSC: 43211708.

In accordance with some embodiments, the other extensions that may be needed to run Infinity Lightpath software for the PC may include USB Touchpad Trackpad, Jelly Comb Ultra Slim Portable Aluminum USB Wired Touchpad with Multi-Touch Navigation for Windows 7/10 PC Laptop Notebook Desktop-TOSS (Silver) Item #T055.

Further, the Infinity Lightpath Program may also require these headphones to be used for either Mac or PC: OneOdio Over Ear Headphone, Wired Bass Headsets with 50 mm Driver, Foldable Lightweight Headphones with Shareport and Mic for Recording Monitoring Podcast Guitar PC TV—(Red).

Figure 25:
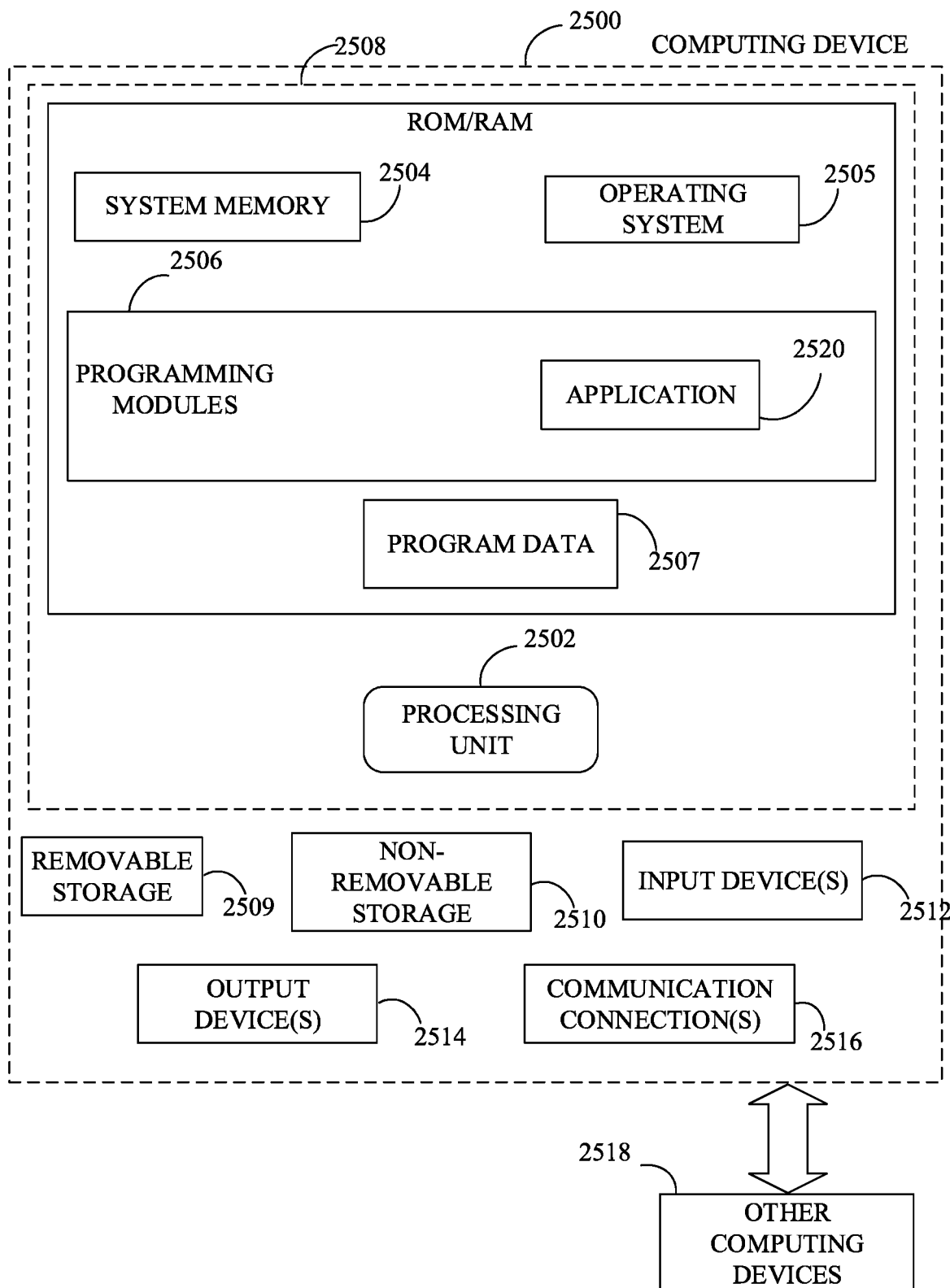
FIG. 25 is a block diagram of a computing device for implementing the methods disclosed herein, in accordance with some embodiments.

With reference to FIG. 25, a system consistent with an embodiment of the disclosure may include a computing device or cloud service, such as computing device 2500. In a basic configuration, computing device 2500 may include at least one processing unit 2502 and a system memory 2504. Depending on the configuration and type of computing device, system memory 2504 may comprise, but is not limited to, volatile (e.g. random-access memory (RAM)), non-volatile (e.g. read-only memory (ROM)), flash memory, or any combination. System memory 2504 may include operating system 2505, one or more programming modules 2506, and may include a program data 2507. Operating system 2505, for example, may be suitable for controlling computing device 2500's operation. In one embodiment, programming modules 2506 may include game module. Furthermore, embodiments of the disclosure may be practiced in conjunction with a graphics library, other operating systems, or any other application program and is not limited to any particular application or system.

This basic configuration is illustrated in FIG. 25 by those components within a dashed line 2508.

Computing device 2500 may have additional features or functionality. For example, computing device 2500 may also include additional data storage devices (removable and/or non-removable) such as, for example, magnetic disks, optical disks, or tape. Such additional storage is illustrated in FIG. 25 by a removable storage 2509 and a non-removable storage 2510. Computer storage media may include volatile and non-volatile, removable and non-removable media implemented in any method or technology for storage of information, such as computer-readable instructions, data structures, program modules, or other data. System memory 2504, removable storage 2509, and non-removable storage 2510 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 2500. Any such computer storage media may be part of device 2500. Computing device 2500 may also have input device(s) 2512 such as a keyboard, a mouse, a pen, a sound input device, a touch input device, a location sensor, a camera, a biometric sensor, etc. Output device(s) 2514 such as a display, speakers, a printer, etc. may also be included. The aforementioned devices are examples and others may be used.

Computing device 2500 may also contain a communication connection 2516 that may allow device 2500 to communicate with other computing devices 2518, such as over a network in a distributed computing environment, for example, an intranet or the Internet. Communication connection 2516 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 2504, including operating system 2505. While executing on processing unit 2502, programming modules 2506 (e.g., application 2520 such as a game player) may perform processes including, for example, one or more stages of methods, algorithms, systems, applications, servers, databases as described above. The aforementioned process is an example, and processing unit 2502 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

What is claimed is:

1. A system for increasing attention ability of a user using a gameplay, the system comprising:
   a display device configured to display a moving image comprising an object, a cursor and a points counter, wherein the object traverses along at least one geometric shape of a plurality of geometric shapes at a predetermined speed and along a predetermined direction, wherein the geometric shape corresponds to a level of a plurality of levels of the gameplay, wherein the displaying of the moving image is based on a video data;
   an audio device configured to produce acoustic waves based on a sound data associated with the level, wherein the production of acoustic waves is synchronous with the display of the moving image;
   an input device configured to receive a spatial input data;
   a processing device communicatively coupled to each of the display device, the audio device and the input device, wherein the processing device is configured to generate the video data and the sound data based on a level indicator of a plurality of level indicators associated with the level and the spatial input data, wherein the processing device is configured to:
      determine a current cursor location associated with the cursor based on each of the spatial input data and a previous cursor location associated with the cursor, wherein each of the current cursor location, the previous cursor location and the spatial input is in relation to a coordinate frame associated with the moving image;
      determine a current object location associated with the object, wherein the object location is in relation to the coordinate frame associated with the moving image;
      determine a distance data representing a distance between the object and the cursor based on a difference between the current cursor location and the current object location;
      analyze the distance data;
      increment a points counter data associated with the points counter based on the analysis of the distance data;
      determine a next object location of the object based on the analysis of the distance data, wherein the next object location is in relation to a coordinate frame associated with the moving image; and
      generate the sound data based on the analysis of the distance data;
   a storage device communicatively coupled to the processing device, wherein the storage device is configured to store digital data corresponding to the object, the cursor, the current cursor location, the previous cursor location, the at least one geometric shape and the sound data in association with the plurality of level indicators;
   wherein the analysis of the distance data comprises comparing the distance data with a predetermined threshold, wherein the next object location of the object is determined to be the current object location based on the distance data being greater the predetermined threshold, wherein the processing device ceases to generate the sound data based on the distance data being greater the predetermined threshold.

2. The system of claim 1, wherein the input device comprises an inertial sensor configured to generate the spatial input data based on a motion imparted to the input device.

3. The system of claim 1, wherein the input device comprises at least one of a mouse, a trackpad and a joy-stick.

4. The system of claim 1, wherein the input device comprises a gaze tracking device configured to detect a gaze of the user in relation to the coordinate frame associated with the moving image, wherein the spatial input is based on the gaze.

5. The system of claim 1, wherein the system comprises a portable computer, wherein each of the display device and the input device is comprised in a touchscreen of the portable computer.

6. The system of claim 1, wherein the processing device is further configured to select the predetermined speed from a plurality of predetermined speeds based on a speed control input, wherein the input device is further configured to receive the speed control input.

7. The system of claim 1, wherein the processing device is further configured to determine laps data representing a number of laps associated with the traversal of the object along the at least one geometrical shape, wherein the display device is further configured to display a laps counter based on the laps data.

8. The system of claim 1, wherein the moving image further comprises a visual rendering of the at least one geometric shape.

9. The system of claim 1, wherein the moving image further comprises a leading object positioned ahead of the object along a direction of the traversal, wherein the leading object traverses the at least one geometric shape.

10. The system of claim 9, wherein the moving image comprises the leading object for a predetermined time duration from a start the gameplay, wherein the leading object fades away subsequent to elapse of the predetermined time duration, wherein the processing device is configured to fade away the leading object based on a fade mode input received from the input device.

11. The system of claim 1, wherein the processing device is further configured to generate the video data and the sound data for a predetermined duration of the gameplay, wherein the predetermined duration of the gameplay is based on a program time input received from the input device.

12. The system of claim 11, wherein the processing device is further configured to generate the video data comprising a countdown timer based on timer data, wherein the processing device is configured for generate the timer data based on time elapsed since beginning of the gameplay.

13. The system of claim 1, wherein the processing device is further configured to generate a simulation mode video data corresponding to the level of the gameplay, wherein the generation of the simulation mode video data is based on a simulation mode control input received from the input device, wherein the object corresponding to the simulation mode video data automatically traverses the at least one geometric shape independent of the spatial input data received subsequent to receiving the simulation mode control input, wherein the processing device is further configured to generate the sound data independent of the spatial input data received subsequent to receiving the simulation mode control input.

14. The system of claim 1, wherein the audio device is configured to generate acoustic waves over a plurality of frequencies comprising 256 Hz, 288 Hz, 323 Hz, 343 Hz, 385 Hz, 432 Hz and 484 Hz respectively corresponding to the plurality of levels of the gameplay.

15. The system of claim 1 further comprising a physiological sensor configured to generate a physiological data of the user, wherein the physiological sensor is communicatively coupled to the processing device, wherein the processing device is further configured to select at least one of the object, the cursor, the at least one geometric shape, the predetermined direction, the predetermined speed and the sound data based on the physiological data.

16. The system of claim 15, wherein the physiological sensor comprises an EEG sensor, wherein the physiological data comprises EEG data, wherein the processing device is further configured to:
analyze the EEG data; and
determine an attention level of the user based on the analysis of the EEG data, wherein the selection of at least one of the object, the cursor, the at least one geometric shape, the predetermined direction, the predetermined speed and the sound data is based on analysis of the EEG data.

17. A system for increasing attention ability of a user using a gameplay, the system comprising:
a display device configured to display a moving image comprising an object, a cursor and a points counter, wherein the object traverses along at least one geometric shape of a plurality of geometric shapes at a predetermined speed and along a predetermined direction, wherein the geometric shape corresponds to a level of a plurality of levels of the gameplay, wherein the displaying of the moving image is based on a video data;
an audio device configured to produce acoustic waves based on a sound data associated with the level, wherein the production of acoustic waves is synchronous with the display of the moving image;
an input device configured to receive a spatial input data;
an EEG sensor configured to generate EEG data of the user;
a processing device communicatively coupled to each of the display device, the audio device and the input device, wherein the processing device is configured to generate the video data and the sound data based on a level indicator of a plurality of level indicators associated with the level and the spatial input data, wherein the processing device is configured to:
determine a current cursor location associated with the cursor based on each of the spatial input data and a previous cursor location associated with the cursor, wherein each of the current cursor location, the previous cursor location and the spatial input is in relation to a coordinate frame associated with the moving image;
determine a current object location associated with the object, wherein the object location is in relation to the coordinate frame associated with the moving image;
determine a distance data representing a distance between the object and the cursor based on a difference between the current cursor location and the current object location;
analyze the distance data;
increment a points counter data associated with the points counter based on the analysis of the distance data;
determine a next object location of the object based on the analysis of the distance data, wherein the next object location is in relation to a coordinate frame associated with the moving image;
generate the sound data based on the analysis of the distance data;
analyze the EEG data;
determine an attention level of the user based on the analysis of the EEG data;
determining the level indicator of the gameplay based on the attention level of the user;
a storage device communicatively coupled to the processing device, wherein the storage device is configured to store digital data corresponding to the object, the cursor, the current cursor location, the previous cursor location, the at least one geometric shape and the sound data in association with the plurality of level indicators.

18. A system for increasing attention ability of a user using a gameplay, the system comprising:
a display device configured to display a moving image comprising an object, a cursor and a points counter, wherein the object traverses along at least one geometric shape of a plurality of geometric shapes at a predetermined speed and along a predetermined direction, wherein the geometric shape corresponds to a level of a plurality of levels of the gameplay, wherein the displaying of the moving image is based on a video data;
an audio device configured to produce acoustic waves based on a sound data associated with the level, wherein the production of acoustic waves is synchronous with the display of the moving image, wherein the audio device is configured to generate acoustic waves over a plurality of frequencies comprising 256 Hz, 288 Hz, 323 Hz, 343 Hz, 385 Hz, 432 Hz and 484 Hz respectively corresponding to the plurality of levels of the gameplay;
an input device configured to receive a spatial input data;
a processing device communicatively coupled to each of the display device, the audio device and the input device, wherein the processing device is configured to generate the video data and the sound data based on a level indicator of a plurality of level indicators associated with the level and the spatial input data, wherein the processing device is configured to:
determine a current cursor location associated with the cursor based on each of the spatial input data and a previous cursor location associated with the cursor, wherein each of the current cursor location, the previous cursor location and the spatial input is in relation to a coordinate frame associated with the moving image;

determine a current object location associated with the object, wherein the object location is in relation to the coordinate frame associated with the moving image;

determine a distance data representing a distance between the object and the cursor based on a difference between the current cursor location and the current object location;

analyze the distance data;

increment a points counter data associated with the points counter based on the analysis of the distance data;

determine a next object location of the object based on the analysis of the distance data, wherein the next object location is in relation to a coordinate frame associated with the moving image; and generate the sound data based on the analysis of the distance data;

a storage device communicatively coupled to the processing device, wherein the storage device is configured to store digital data corresponding to the object, the cursor, the current cursor location, the previous cursor location, the at least one geometric shape and the sound data in association with the plurality of level indicators;

wherein the analysis of the distance data comprises comparing the distance data with a predetermined threshold, wherein the next object location of the object is determined to be the current object location based on the distance data being greater the predetermined threshold, wherein the processing device ceases to generate the sound data based on the distance data being greater the predetermined threshold.

* * * * *